(12) United States Patent
Nataraj et al.

(10) Patent No.: US 11,744,969 B2
(45) Date of Patent: Sep. 5, 2023

(54) MECHANICAL VENTILATOR APPARATUSES AND METHODS THEREOF

(71) Applicant: Villanova University, Villanova, PA (US)

(72) Inventors: Chandrasekhar Nataraj, Chadds Ford, PA (US); Alfonso Ortega, Villanova, PA (US); Garrett Clayton, Villanova, PA (US); Christopher Townend, Villanova, PA (US)

(73) Assignee: VILLANOVA UNIVERSITY, Villanova, PA (US)

( * ) Notice: Subject to any disclaimer, the term of this patent is extended or adjusted under 35 U.S.C. 154(b) by 0 days.

(21) Appl. No.: 17/412,712

(22) Filed: Aug. 26, 2021

(65) Prior Publication Data

US 2022/0062571 A1 Mar. 3, 2022

Related U.S. Application Data

(60) Provisional application No. 63/070,467, filed on Aug. 26, 2020.

(51) Int. Cl.
*A61M 16/00* (2006.01)
*A61M 16/20* (2006.01)
(Continued)

(52) U.S. Cl.
CPC ...... *A61M 16/024* (2017.08); *A61M 16/0003* (2014.02); *A61M 16/0051* (2013.01);
(Continued)

(58) Field of Classification Search
CPC ..................................... A61M 16/0072–0084
See application file for complete search history.

(56) References Cited

U.S. PATENT DOCUMENTS 3,552,380 A * 1/1971 Heldt .................. A61M 16/04
                                                          131/330
3,757,776 A * 9/1973 Bauman ............ A61M 16/0057
                                                          128/205.13
(Continued)

FOREIGN PATENT DOCUMENTS

WO      20190043146 A      4/2019
WO      2019229776 A1     12/2019
WO   WO-2021220234 A1 *  11/2021

OTHER PUBLICATIONS

International Search Report and Written Opinion for PCT/US21/47680, dated Dec. 10, 2020.

*Primary Examiner* — Michael J Tsai
(74) *Attorney, Agent, or Firm* — Troutman Pepper Hamilton Sanders LLP (Rochester)

(57) ABSTRACT

A ventilator apparatus includes a linear electro-mechanical actuator that interfaces with a self-inflating bag including an inlet configured to receive air and an outlet configured to expend the air. A three-way valve is coupled to the outlet via a first flowmeter, an ambient environment via a second flowmeter, and a patient via an endotracheal tube. The first and/or second flowmeters are coupled to pressure transducer(s). A control unit is coupled to the linear electro-mechanical actuator and the first and second flowmeters and includes a control panel, memory including programmed instructions stored thereon, and processor(s) configured to execute the stored programmed instructions to set an inhalation time and an exhalation time. A current inspiratory pressure and a current tidal volume are obtained from the pressure transducer(s) and/or the first flowmeter. A stroke of the linear electro-mechanical actuator is then controlled to facilitate inspiratory and expiratory phases of a respiratory cycle.

21 Claims, 24 Drawing Sheets

(51) Int. Cl.
*A61M 16/10* (2006.01)
*A61M 16/04* (2006.01)

(52) U.S. Cl.
CPC ...... *A61M 16/0084* (2014.02); *A61M 16/105* (2013.01); *A61M 16/208* (2013.01); *A61M 16/0465* (2013.01); *A61M 2016/0027* (2013.01); *A61M 2016/0036* (2013.01); *A61M 2205/3334* (2013.01); *A61M 2206/20* (2013.01); *A61M 2230/42* (2013.01)

(56) References Cited

U.S. PATENT DOCUMENTS

| | | | | |
|---|---|---|---|---|
| 3,818,806 | A * | 6/1974 | Fumagalli | A61M 16/0057 74/48 |
| 3,964,476 | A * | 6/1976 | Palleni | A61M 16/08 128/205.24 |
| 4,706,683 | A * | 11/1987 | Chilton | A61M 15/02 128/203.29 |
| 5,803,074 | A * | 9/1998 | Pope | A61M 16/0084 128/205.24 |
| 6,058,787 | A * | 5/2000 | Hughes | G01F 1/74 73/861.66 |
| 6,155,257 | A * | 12/2000 | Lurie | A61H 31/006 128/205.24 |
| 6,339,963 | B1 * | 1/2002 | Torkildsen | G01F 7/005 73/861.63 |
| 6,463,810 | B1 * | 10/2002 | Liu | G01F 1/44 73/861.63 |
| 6,772,754 | B1 * | 8/2004 | Mendenhall | A61M 16/208 128/207.14 |
| 8,534,282 | B2 * | 9/2013 | Bergman | A61M 16/0078 128/205.16 |
| 10,912,903 | B2 * | 2/2021 | Fried | A61M 16/00 |
| 11,253,664 | B2 * | 2/2022 | Molander | A61M 16/0051 |
| 2005/0284472 | A1 * | 12/2005 | Lin | A61M 16/0084 128/202.29 |
| 2007/0125377 | A1 * | 6/2007 | Heinonen | A61M 16/203 128/204.21 |
| 2010/0191481 | A1 * | 7/2010 | Steven | G01F 1/44 340/626 |
| 2011/0041852 | A1 * | 2/2011 | Bergman | A61M 16/0078 128/205.13 |
| 2012/0145151 | A1 * | 6/2012 | Bergman | A61M 16/0084 128/205.16 |
| 2013/0125893 | A1 * | 5/2013 | Peace | A61M 16/0078 128/205.12 |
| 2014/0000613 | A1 * | 1/2014 | Hines | A61M 16/0081 128/205.16 |
| 2017/0197047 | A1 * | 7/2017 | Minato | A61M 16/0051 |
| 2017/0216549 | A1 * | 8/2017 | Chang | A61M 16/022 |
| 2019/0036713 | A1 | 1/2019 | Slik | |
| 2019/0232016 | A1 * | 8/2019 | Sayani | A61M 16/0003 |
| 2019/0336713 | A1 * | 11/2019 | Piracha | A61M 16/0078 |
| 2020/0086075 | A1 * | 3/2020 | Mujeeb-U-Rahaman | A61M 16/06 |
| 2020/0261672 | A1 * | 8/2020 | Pasupuleti | A61M 16/0081 |
| 2020/0353192 | A1 * | 11/2020 | Fried | A61M 16/0051 |
| 2021/0322692 | A1 * | 10/2021 | Molander | A61M 16/201 |
| 2021/0330914 | A1 * | 10/2021 | Young | G06N 3/126 |

* cited by examiner

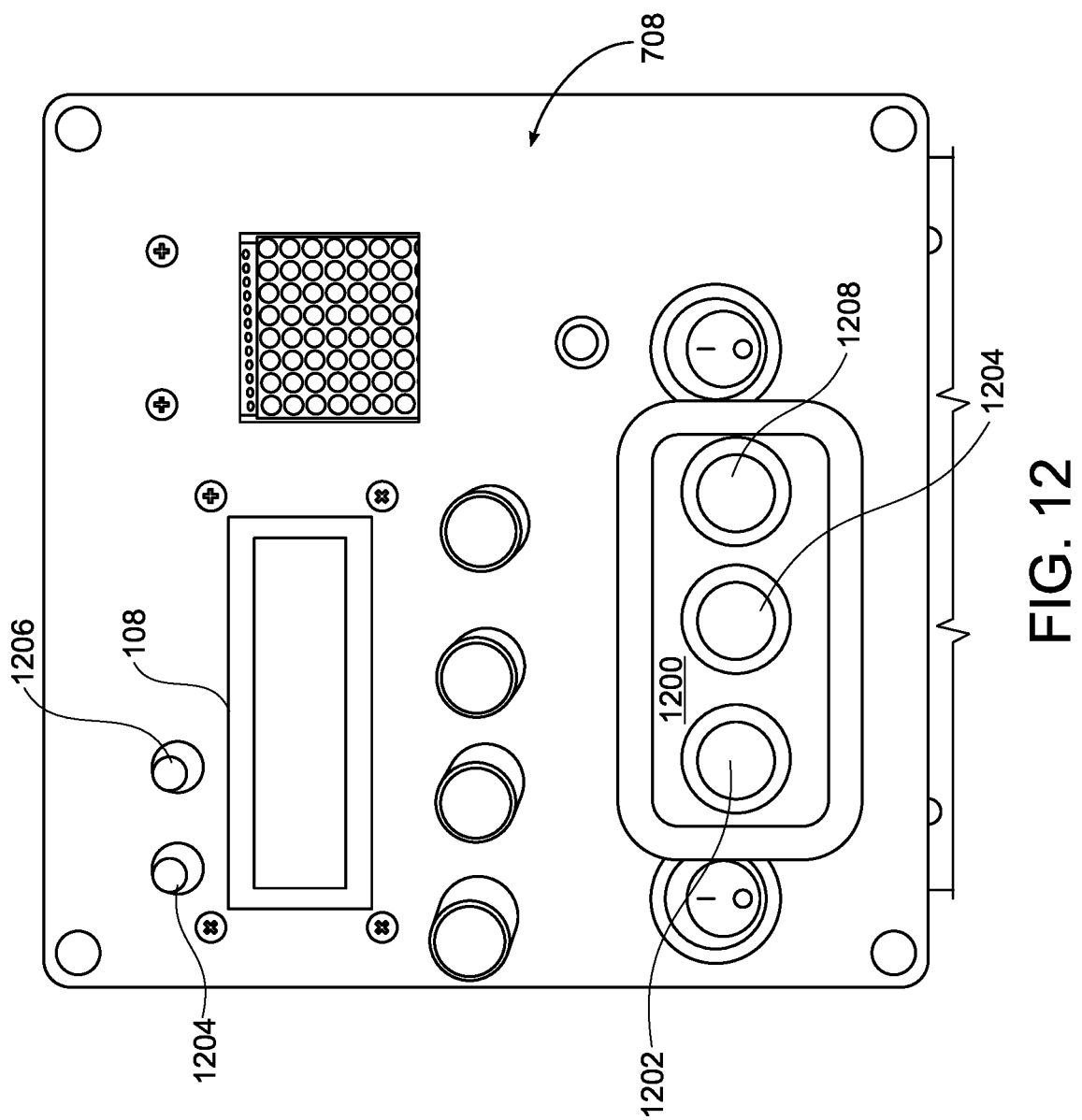

| Row | Property | Guide Word | Deviation | Cause | Consequences | Action |
|---|---|---|---|---|---|---|
| 1 | Pressure | More | More pressure in gas inlet | Case 1: If O2 or O2/air mixture, O2 line pressure regulator valve (PRegV) in supply line doesn't work properly<br>Case 2: If air only, not possible | Case 1: Pressure>Pmax, high pressure in inspiration line | Case 1: O2 excess line valve operates and avoid high pressure in inspiration line. In addition high pressure alarm alerts clinician. |
| 2 | Pressure | Less | Less pressure in gas inlet | Case 1: If O2 or O2/air mixture - PRegV in supply line doesn't work properly OR Pressure drop in the supply line due to high consumption of other consumers<br>Case 2: If air only, not possible | The AMBU bag is filled more (or totally) with ambient air and the process continues with less (or no) pure O2. | Case 1: We are not noticing the O2 fraction of mixed air has dropped, but it is not a critical issue. We won't sense it locally but the clinician will see that in O2 saturation. |
| 3 | Flow | No | No flow in gas inlet | Case 1: Inlet valve closed/blocked<br>Case 2: The AMBU bag is filled. | Case 1: The AMBU bag is not filled<br>Case 2: No problem | Case 1: Low volume Alarm<br>Case 2: No problem |
| 4 | Flow | More | More flow in gas inlet | Not possible | | |
| 5 | Flow | Less | Less flow in gas inlet | Case 1: Inlet valve partially closed/blocked<br>Case 2: The AMBU bag is filled. | Case 1: The AMBU bag is not filled<br>Case 2: No problem | Case 1: Low volume Alarm<br>Case 2: No problem |
| 6 | Flow | Reverse | Reserve flow in gas inlet | Case 1: If air only, leakage of air inlet check-valve<br>Case 2: If O2 or O2/air mixture, not possible | Case 1: AMBU bag is not filled sufficiently. | Case 1: Low volume Alarm. |

FIG. 13A

| 7* | Temper ature | More | High gas temperature | Not possible | | |
|---|---|---|---|---|---|---|
| 8* | Temper ature | Less | Low gas temperature | Not possible | | |
| 9 | Compos ition | Part of | Solid particles | Foreign material in O2 supply lines/hose or dust in the air | Particle goes to inspiration line | HEPA (or B/V) filter operates and does not allow particles to go to the patient lungs |
| 10* | Compos ition | less | Humidity | Not possible; | | The O2 itself is dry. No way to have less humid O2 |
| 11* | Compos ition | high | Humidity | Not possible; | | The O2 itself is dry. No way to have less humid O2 |

FIG. 13A (continued)

| Row | Property | Guide Word | Deviation | Cause | Consequences | Action |
|---|---|---|---|---|---|---|
| 1 | Pressure | More | More pressure in AMBU bag outlet | 1- Controller Problem<br>2- Actuator Problem<br>3- O2 excess valve blockage | Pressure>Pmax, high pressure in inspiration line | 1- Pressure release valve (PRelV) operates and avoid high pressure in inspiration line<br>2- Pop-up valve activated alarm<br>3- If PRelV for any reason doesn't decrease the pressure enough, PT sends high pressure signal to controller and we will have also high pressure alarm and indicator light |
| 2 | Pressure | Less | No Problem | | Less pressure is not a problem as long as we have enough flow that results in adequate volume delivered | If less pressure results in low flow that results in insufficient volume, then volume alarm and indicator light |
| 3** | Flow | No | No flow in AMBU bag outlet | 1- Controller Problem<br>2- Actuator Problem<br>3- O2 excess valve leakage<br>4- Check valve leakage<br>5- AMBU bag leakage | No inspiration flow | Volume alarm and indicator light |
| 4 | Flow | More | More flow in AMBU bag outlet | 1- Actuator Problem<br>2- Controller Problem<br>3- Temporary sticking the AMBU bag outlet valve and suddenly opening | More inspiration flow itself is not the problem but delivery of excess volume to the patient is a problem. | Flow-meter sends more-flow signal to controller and the controller reacts and/or volume alarm and indicator light |

FIG. 13B

| | | | | | |
|---|---|---|---|---|---|
| 5** | Flow | Less | Less flow in AMBU bag outlet | 1- Controller Problem<br>2- Actuator Problem<br>3- O2 excess valve leakage<br>4- Check valve leakage<br>5- AMBU bag leakage | Insufficient volume | Volume alarm and indicator light |
| 6 | Flow | Reverse | Reverse flow in AMBU bag outlet | Case 1: The duck-valve leakage in expiration step when the AMBU bag is filling up | Case 1- Expiration air does not completely exit the ventilator and reused and it builds up CO2 (rebreathing) | Case 1- If there is CO2 sensor in the patient monitoring system, it will display inspired CO2 or alarm, otherwise the it will cause O2 desaturation which will alarm. Both of these alarms are in the patient monitoring system and not in NovaVent system. Increased oxygen inflow may compensate. |
| | | | | Case 2: PRelV leakage | Case 2- Inspired volume decreased. | Case 2- If large, will alarm on low volume or low pressure. |
| 7 | Temperature | More | | Not Important | | |
| 8 | Temperature | Less | | Not Important | | |
| 9 | Composition | Part of | Solid particles | Foreign material in O2 supply lines/hose; Dust in air | Particle goes to inspiration line | HEPA (or B/V (bacterial/viral)) filter operates and does not allow particles to go to the patient lungs |
| 10 | Composition | Less | Humidity | If the mixed air is totally or mostly O2 | decrease the humidity of inspiration air | Ensure humidification (active or passive) is present in the inspiratory line. |
| 11 | Composition | High | Humidity | Not possible | | |

FIG. 13B (continued)

| Row | Property | Guide Word | Deviation | Cause | Consequences | Action |
|---|---|---|---|---|---|---|
| 1 | Pressure | More | More pressure in inspiration line | Not possible (PRelV in AMBU bag outlet has been already activated) | High pressure inspiration flow | If PRelV for any reason doesn't decrease the pressure enough, we have high pressure alarm |
| 2 | Pressure | Less | Less pressure in inspiration line | 1- HEPA (or B/V) filter blockage 2- Expiration valve leakage 3- Tube leakage 4- Controller Problem 5- Actuator Problem | 1- Low inspiration pressure | Low pressure is not a problem as long as we have enough flow |
| 3** | Flow | No | No flow in inspiration line | 1- HEPA (or B/V) filter blockage 2- Expiration valve leakage 3- Tube leakage 4- PRelV leakage 5- Controller/Actuator Problem | No inspiration flow | Volume alarm |
| 4 | Flow | More | More flow in inspiration line | 1- Actuator Problem 2- Controller Problem 3- Temporary stucking the AMBU bag outlet valve and suddenly opening | More inspiration flow itself is not the problem but delivery of excess volume to the patient is a problem. | Flow-meter sends more-flow signal to controller and the controller reacts and/or volume alarm |

FIG. 13C

| | | | | Low inspiration flow | Volume alarm |
|---|---|---|---|---|---|
| 5** | Flow | Less | 1- HEPA (or B/V) filter blockage<br>2- Expiration valve leakage<br>3- Tube leakage<br>4- Controller Problem<br>5- Actuator Problem | | |
| 6 | Flow | Reverse | When the patient exhales we will have reverse flow in the expiration line and it is OK | | |
| 7 | Temperature | More | Not Important | | |
| 8 | Temperature | Less | Not Important | | |
| 9 | Composition | Part of | Not Possible | | HEPA filter already filtered the inspiration air |
| 10 | Composition | Less | If the mixed air is totally or mostly O2 | decrease the humidity of inspiration air | Ensure humidification (active or passive) is present in the inspiratory line. |
| 11 | Composition | High | Not possible | | |

FIG. 13C (continued)

| Row | Property | Guide Word | Deviation | Cause | Consequences | Action |
|---|---|---|---|---|---|---|
| 1 | Pressure | More | More pressure in expiration line | PEEP valve or flowmeter failed/blocked | Breathing process problem/failure | We have no way currently for the system to know the PEEP setting, but if PEEP goes above 20 cmH2O, an alarm will sound to alert the clinician. |
| 2 | Pressure | Less | Less pressure in expiration line | Peep valve problem | The patient lung will collapse | We have no way currently for the system to know the PEEP setting, but if PEEP goes below 5 cmH2O, an alarm will sound to alert the clinician. |
| 3 | Flow | No | No flow in expiration line | 1- Peep-valve blockage 2- Line blockage 3- Duck-valve stuck shut 4- HEPA filter blocked | Cases1&2&4: No expiration flow Case 3: the patient cannot exhale | If the clinician is present, they will see the low flow on the flow-volume diagram. If the clinician is not present, this will eventually create high pressure which will result in an alarm. |
| 4 | Flow | More | More flow in expiration line | The AMBU bag is not sufficiently compressed and the duck-valve will be stuck in the mid-point. | less inspiration flow | Low volume alarm (inspiration flowmeter) Or the controller will react and solve that. |

FIG. 13D

| | | | | | |
|---|---|---|---|---|---|
| 5 | Flow | Less | Less flow in expiration line | 1- Peep-valve partially blockage 2- Line partially blockage 3- Duck-valve stuck shut partially 4- HEPA (or B/V) filter partially blocked | Cases1&2&4: low expiration flow Case 3: the patient can exhale but some of the exhalation will go to AMBU bag | If the clinician is present, they will see the low flow on the flow-volume diagram. If the clinician is not present, this will eventually create high pressure which will result in an alarm. |
| 6 | Flow | Reverse | Reverse flow in expiration line | Not possible | | |
| 7 | Temperature | More | | Not important | | |
| 8 | Temperature | Less | | Not important | | |
| 9 | Composition | Part of | Solid particles in supplied O2 | Not possible | | |
| 10 | Composition | Part of | Humidity | Not important | Exhalation of the patient | |
| 11 | Composition | Part of | Virus | | Spreads the virus in the room | HEPA filter will attenuate viral emission. |

| Part Description | Material | Vendor | Part Number/ | Qty | Notes |
|---|---|---|---|---|---|
| Frame/ Enclosure | | | | | |
| Ambu Bag/ Actuator Frame | Polycarbonate, 1/2" | Mc Master-Carr | 8574K45 | 2 | Cut and machined to 12x20 and 12 x 7 |
| Actuator / Electronics enclosure | HD Polyethylene, 3/8" | Mc Master-Carr | 8619K434 | 1 | Cut and machined to 13x7 and 12 x 7 |
| Actuator / Electronics enclosure | HD Polyethylene, 1/2" | Mc Master-Carr | 8619K471 | 1 | Cut and machined to 12 x 7 |
| Linear Actuator, 4" Stroke, 100 Lb. Force | Aluminum,Steel, ABS | Progressive Automations | PA-04-4-100 | 1 | |
| Switched Power entry, IEC 14C | ABS | Digikey | 486-2246-ND | 1 | Shurter Electronics # DC11.0001.001 |
| Handles | Stainless Steel | Mc Master-Carr | 7088A71 | 2 | |
| Hinges | Stainless Steel | Mc Master-Carr | 1586A41 | 2 | |
| Wraparound Cleat | Nylon | Mc Master-Carr | 33805T34 | 1 | |
| Knurled-Head Thumb Nuts, 10-32 | Stainless Steel | Mc Master-Carr | 95150A160 | 6 | |
| Tubing 1/8" ID x 1/4" OD, cut to 2 ft. Length | Nylon | McMaster-Carr | 5233K52/ 50ft | 6 | |
| Tube adapters 1/8" x 1/16" | Acetal Plastic | Mc Master-Carr | 5047K24 | 8 | |
| Y connections, 1/8" ID Tube | Polypropylene | Mc Master-Carr | 5463K118 | 2 | |
| Instrumentation | | | | | |
| Arduino UNO R3 Microcontroller | E-glass/ metal | Amazon | B008GRTSV6 | 1 | |
| Motor Driver, Bi-directional, 10A | E-glass/ metal | Amazon | B01M5I2NFM | 1 | MDD10A https://www.cytron.io/p-10amp-5v-30v-dc-mo |
| Terminal Strip Blocks with Cover, 6 Positions | Poly Carbonate/ tinned copper | Amazon | B07CLY5N9T | 2 | |
| UI Control Box, 6" x 6: x 3" | ABS | Amazon | B07G4R5YV4 | 1 | |
| Display, LCD: 16x2 | E-glass | Amazon | B00HJ6AFW6 | 1 | |
| LED Array, Dot Matrix Module | E-glass | Amazon | B079NJLGMG | 1 | |
| Potentiometers, | Metal + Carbon Film | Amazon | B07QMR2L2B | 4 | |
| Switches | Polycarbonate | Amazon | B07QG1W93X | 2 | |
| Buttons, Recessed Momentary | Polycarbonate | Amazon | B073VTQ7B9 | 3 | |
| LED Holder | Copper | Amazon | B07D9JL55L | 2 | |
| Ethernet feed thru | ABS/ E-Glass | aliexpress.com | 32678175366 | 2 | https://www.aliexpress.com/item/32678175366.html?spr |
| dPp Trnsdcrs +/-5kPa, NXP Semiconductor | PPS | Mouser | 841-MP3V5004DP | 4 | |
| Piezo Buzzers, 2./3KHz, 85 dB | PPS | Mouser | 497-1E122303-1 | 1 | |
| Molex Quick connect Male | Nylon | McMaster-Carr | 69295K65 | 1 | |
| Molex Quick connect Female | Nylon | McMaster-Carr | 69295K85 | 1 | |
| Molex Male pin | Tinned Copper | McMaster-Carr | 69295K23 | 1 | |
| Molex Female pin | Tinned Copper | McMaster-Carr | 69295K33 | 1 | |
| Hose Barb | Nickel Plated Brass | McMaster-Carr | 2844K13 | 12 | |
| Flow Meter Assembly (2 req) | | | | | |
| Machnd/3D Pmt Bi-Dir. Flowmeter Insert | Mult. 1.25 OD Stainless Rod | McMaster-Carr/ Shop | 89535K45 | 2 | Can be Stainless Steel (89535K45) or Medical grade Plastic |
| Machnd/3D Pmt- 20mm Male Hose-end Insert | Mult. 1.25 OD Stainless Rod | McMaster-Carr | 89535K45 | 1 | As require by hose termination, 3D Print: PC/ABS or Nylon |
| Machnd/3D Pmt20mm Female Hose-end/ PEEP | Mult. 1.25 OD Stainless Rod | McMaster-Carr | | 3 | As require by hose termination, PEEP Adapter |
| 1" ID Tube or pipe | Sch 40 PVS Pipe or SS | McMaster-Carr/ SS | | 1 | Cut to 88mm long, 3) holes, D&T 10-32 thread |
| O-rings, Size #20, 1" OD x 7/8" ID x 1/16"CS | Silicone | McMaster-Carr | 89895K771 | 12 | |
| Hose Barb | Nickel Plated Brass | McMaster-Carr | 1283N32 | 6 | |
| Tubing 1/8" ID x 1/4" OD, cut to 6ft. Length | Nylon | McMaster-Carr | 2844K13 | 6 | Substitute with Medical Grade |
| | | | 5233K52/ 50ft | | |
| Provided by End User | | | | | |
| Resuscitator with Reservoir Bag | Plastic/ rubber | AED Super Store/ equiv | SB28521U | 1 | |
| PEEP Valve, Disposable | PolySulfone | AED Super Store/ equiv | 8501 | 1 | |
| 2Mtr I/E hose | | | | 2 | |

FIG. 16A

| Tidal Volume \ Respiratory Rate | 10 | 12 | 14 | 16 | 18 | 20 | 22 | 24 | 26 | 28 | 30 |
|---|---|---|---|---|---|---|---|---|---|---|---|
| 250 | | | | | | | | | | | |
| 300 | | | | | | | | | | | |
| 350 | | | | | | | | | | | |
| 400 | | | | | | | | | | | x |
| 450 | | | | | | | | | | x | 411 |
| 500 | | | | | | x | | | | 500 | |
| 550 | | | | | | | | | | 559 | |
| 600 | | | | | | | | | x | | |
| 650 | | | | | | | | | 691 | | |
| 700 | | | | | | | | x | | | |
| 750 | | | | | | | | 720 | | | |
| 800 | x | | x | | x | | x | | | | |

| Tidal Volume \ Respiratory Rate | 10 | 12 | 14 | 16 | 18 | 20 | 22 | 24 | 26 | 28 | 30 |
|---|---|---|---|---|---|---|---|---|---|---|---|
| 250 | | | | | | | | | | | |
| 300 | | | | | | | | | | | x |
| 350 | | | | | | | | | | | 242 |
| 400 | | | | | | | | | x | | |
| 450 | | | | | | | | | 296 | | |
| 500 | | | | | | | | x | | | |
| 550 | | | | | | | | 330 | | | |
| 600 | | | | | | | x | | | | |
| 650 | | | | | | | 392 | | | | |
| 700 | | | | | | x | | | | | |
| 750 | | | | | x | 430 | | | | | |
| 800 | x | | | | 550 | | | | | | |
|  | | | | | 550 | | | | | | |
|  | | | x | 650 | | | | | | | |
|  | | x | | | | | | | | | |

708

US 11,744,969 B2

MECHANICAL VENTILATOR APPARATUSES AND METHODS THEREOF

This application claims the benefit of U.S. Provisional Patent Application Ser. No. 63/070,467, filed Aug. 26, 2020, which is hereby incorporated by reference in its entirety.

FIELD

This technology generally relates to ventilator devices and, more particularly, to mechanical ventilator apparatuses with reduced complexity for emergency deployments in clinical environments and methods thereof.

BACKGROUND

Currently available mechanical ventilators are complex medical devices that pump air and oxygen into the lungs and remove carbon dioxide, assisting patients whose lungs otherwise cannot function adequately. The most critically ill COVID-19 patients, for example, develop severe pneumonia, and often need ventilators to survive and recover. There is a dire need for ventilators in many developing countries where demand can quickly exceed limited supply.

However, current ventilators are relatively expensive, complex, and difficult and time-consuming to manufacture. In particular, current ventilators have more modes than necessary for treating limited conditions often seen in viral infections (e.g., COVID-19). Additionally, current ventilators have many parts and associated supply chain dependencies. Accordingly, current ventilators are unable to effectively meet current needs, particularly for emergency deployments to treat severe patient conditions in underserved and geographically remote populations.

SUMMARY

A ventilator apparatus is disclosed that in some examples includes a linear electro-mechanical actuator configured to operatively interface with a self-inflating bag that comprises an inlet configured to receive air and an outlet configured to expend the received air. The ventilator apparatus in these examples further includes a three-way valve coupled to the outlet of the self-inflating bag via at least a first flowmeter, an ambient environment via at least a second flowmeter, and a patient via at least an endotracheal tube. One or more of the first or second flowmeters are coupled to one or more pressure transducers. A control unit is communicably coupled to the linear electro-mechanical actuator and the first and second flowmeters and includes a control panel, memory comprising programmed instructions stored thereon, and one or more processors configured to execute the stored programmed instructions to set an inhalation time and an exhalation time based on parameter values obtained via the control panel. At least a current inspiratory pressure and a current tidal volume are obtained from one or more of the pressure transducers or the first flowmeter. A stroke of the linear electro-mechanical actuator is then selectively controlled, based on the inhalation and exhalation times and a comparison of the current inspiratory pressure and the current tidal volume with one or more of the parameter values, to facilitate inspiratory and expiratory phases of a respiratory cycle for the patient.

In another example, a method for facilitating a respiratory cycle, and implemented by a control unit of a ventilator apparatus, is disclosed that includes setting an inhalation time and an exhalation time based on obtained parameter values comprising at least an inspiratory pressure limit and a required tidal volume. At least a current inspiratory pressure and a current tidal volume are obtained from one or more pressure transducers or a first flowmeter. The first flowmeter is disposed between a self-inflating bag and a three-way valve and is coupled to one or more of the pressure transducer. A stroke of a linear electro-mechanical actuator is selectively controlled, based on the inhalation and exhalation times and a comparison of the current inspiratory pressure and the current tidal volume with one or more of the parameter values, to facilitate inspiratory and expiratory phases of a respiratory cycle for the patient.

In yet other examples, a method of making a ventilator apparatus is disclosed that includes placing a self-inflating bag into a cradle disposed within an enclosure. The self-inflating bag includes an inlet configured to receive air and an outlet configured to expend the received air. A three-way valve is coupled to the outlet of the self-inflating bag via at least a first flowmeter in an inspiratory flow path, an ambient environment via at least a second flowmeter in an expiratory flow path, and a patient via at least an endotracheal tube in the inspiratory flow path. One or more pressure transducers are inserted into one or more of the first or second flowmeters. A linear electro-mechanical actuator is then attached to the enclosure proximate the self-inflating bag. The linear electro-mechanical actuator is configured to operatively engage with, and disengage from, the self-inflating bag. A control unit is communicably coupled to the linear electro-mechanical actuator and one or more of the pressure transducers or first or second flowmeters. The control unit is configured to selectively control a stroke of the linear electro-mechanical actuator to facilitate inspiratory and expiratory phases of a respiratory cycle for a patient.

The technology disclosed herein provides an elegant, efficient, and cost-effective mechanical ventilator that requires reduced complexity and a reduced number of parts. Accordingly, the mechanical ventilator is less reliant on extensive supply chains and can be manufactured more quickly and in more remote and other environments and geographic regions in which parts may be more difficult to obtain. The mechanical ventilator can operate using ventilator circuits already in hospitals and other clinical environments to facilitate respiration for patients in emergency conditions and respiratory distress, such as due to significant viral infection.

BRIEF DESCRIPTION OF THE DRAWINGS

FIG. 12 is a diagram illustrating exemplary alarm outputs of a ventilator apparatus;

FIGS. 13A-D are tables of exemplary failure scenarios and resulting actions, including particular triggered alarm(s), relating to the bag-mask-valve gas inlet, mechanical air-pump outlet, inspiration line outlet, and expiration line outlet, respectively;

FIG. 14 is a table including exemplary components of a ventilator apparatus;

FIGS. 16A-C are graphs of exemplary performance of a ventilator apparatus with respect to respiratory rate and tidal volume.

DETAILED DESCRIPTION

Figure 1:
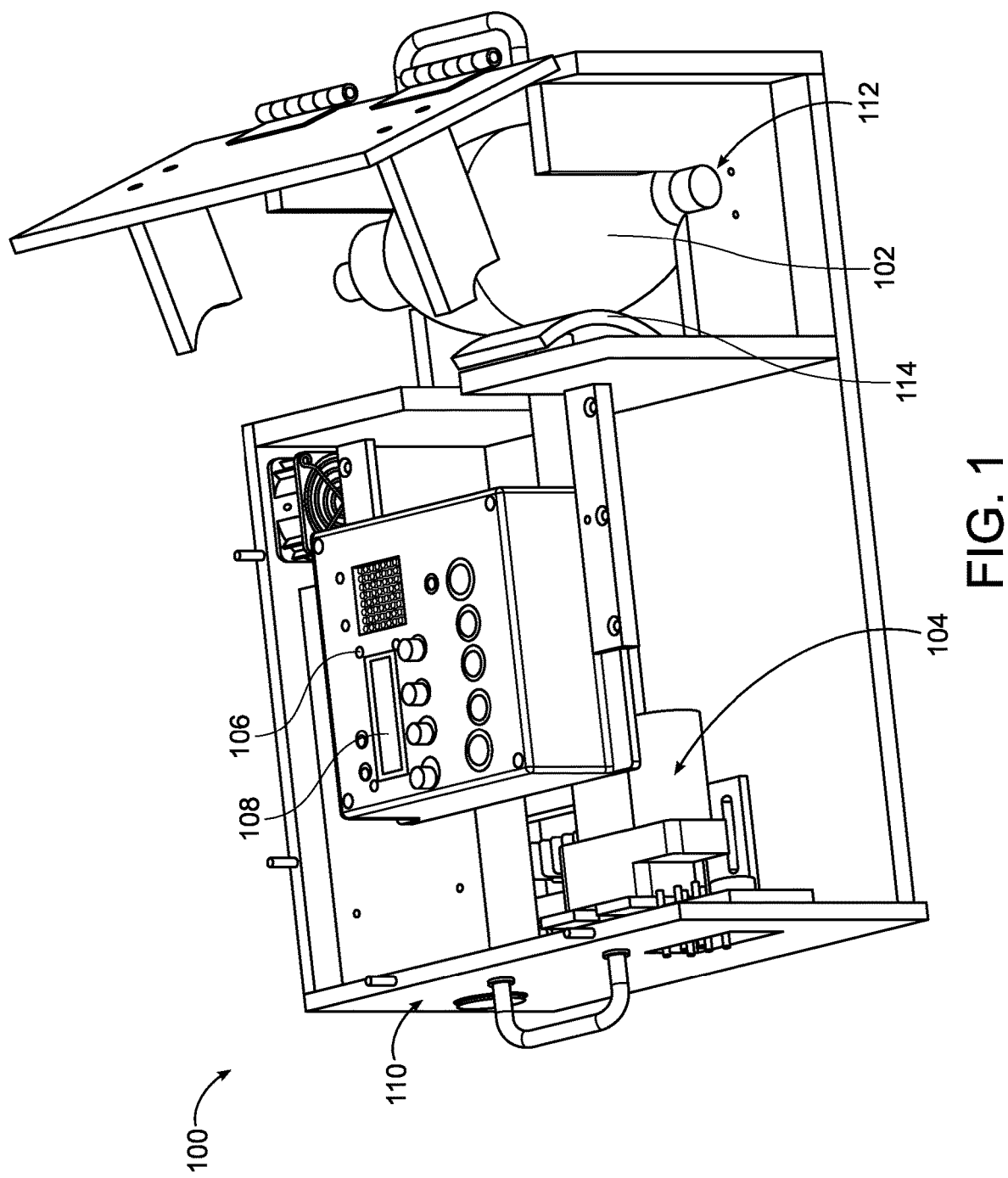
FIG. 1 is a perspective view of an exemplary ventilator apparatus.
Figure 2:
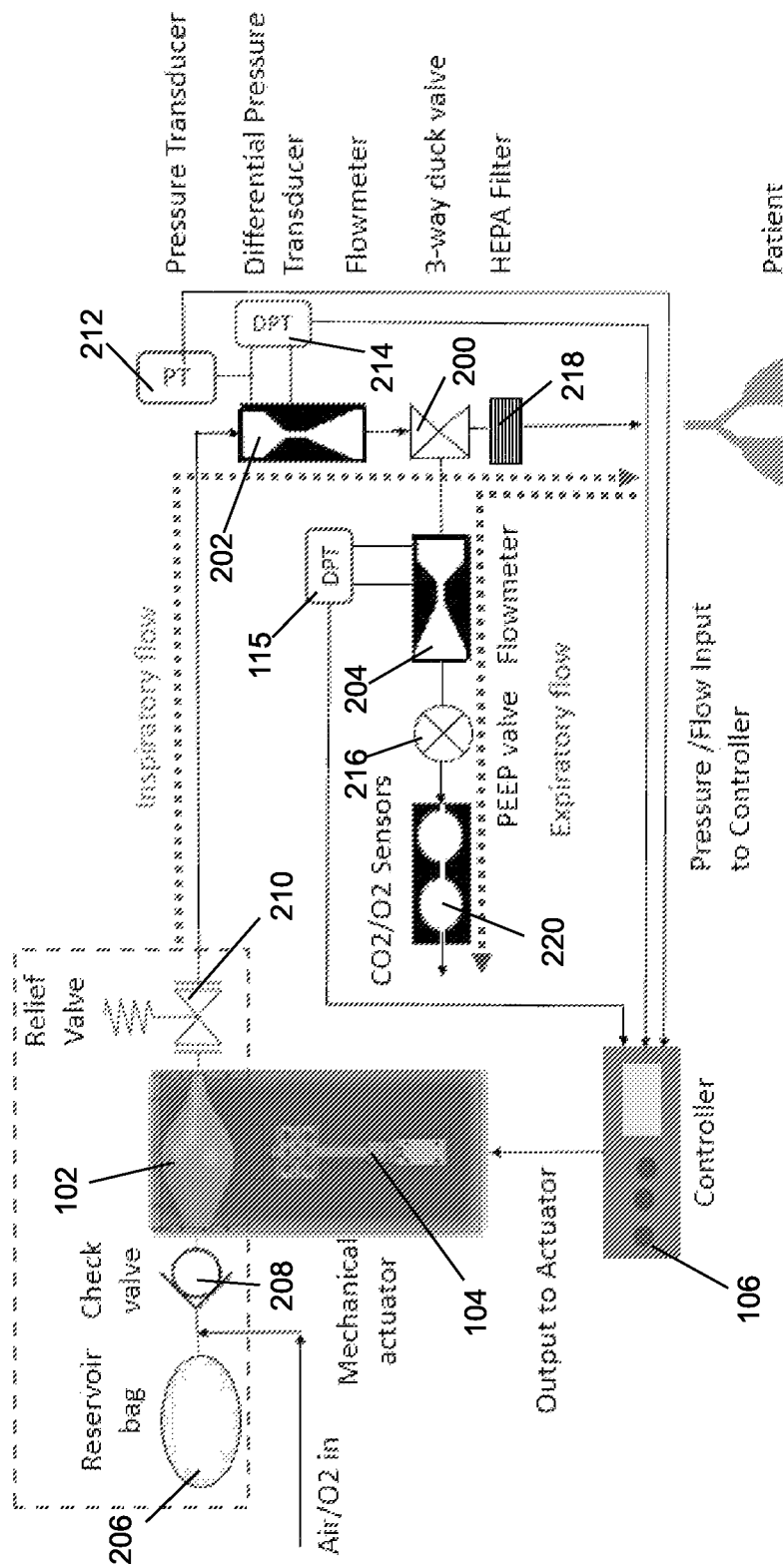
FIG. 2 is flow diagram illustrating an exemplary operation of a ventilator apparatus.

Referring to FIGS. 1-2, a perspective view of an exemplary ventilator apparatus 100, and a flow diagram of an exemplary operation of the ventilator apparatus 100, according to some examples of this technology are illustrated, respectively. The ventilator apparatus 100 described and illustrated by way of the examples herein is configured to operate with ventilator circuits already in hospitals and other medical environments. Examples of the ventilator apparatus 100 are focused on the typical need in COVID-19 and other patients with respiratory distress: operating in continuous mandatory ventilation (CMV) mode, with controllable inspiration/expiration (I/E) ratio, breaths per minute (BPM), tidal volume (TV), and inspiratory pressure limit. However, in some examples, other modes of operation can also be utilized, as described in more detail below.

The operation of the ventilator apparatus 100 includes mechanically compressing a self-inflating bag 102 (e.g., an artificial manual breathing unit (AMBU™) bag or bag included in a bag-valve-mask (BVM) device with an electromechanical linear actuator 104. Medical grade valves, including 3-way valve 200, regulate both the inspiration and expiration flow rates and ensure minimum pressures. Flowmeters 202 and 204 are used with a control unit 106 that can include a microcontroller programmed to regulate the flow. The control unit 106 permits a clinician to select key parameters via a manual control panel. A display device 108 is integrated into the control unit 106 for essential parameters as well as a graphical flow-volume diagram that serves as valuable input to the clinician to assess the performance of the ventilator apparatus 100, and to gauge the current condition of the patient.

Accordingly, the ventilator apparatus 100 of this technology is a microcontroller-driven actuating system configured to be mated to a ventilator circuit (e.g., an FDA-approved ventilator circuit). The ventilator apparatus 100 includes a self-inflating bag 102 connectable to a ventilator hose that connects to an endotracheal tube (ETT) (not shown). The ventilator apparatus 100 is configured to operate in a volume control mode and can be provided to a patient who is in a sedated mode and/or a mode in which the patient is not breathing on their own. The ventilator apparatus 100 of this technology can advantageously operate in an emergency mode providing urgent ventilation when so indicated, as well as other modes and explained in more detail below.

The ventilator apparatus 100 is configured to be deployed in a monitored hospital or other clinical environment and its operation can be managed by trained clinical personnel with supportive ancillary services, for example, although other types of deployments can also be used. Traditional sensors (such as pulse oximeters, cardiac monitors, oxygen concentration, carbon dioxide concentration, etc.) are generally available in a clinical setting and could be used in conjunction with the control unit 106 and display device 108 of the ventilator apparatus 100 to make clinical decisions.

The ventilator apparatus 100 includes a housing 110 or enclosure that supports the self-inflating bag 102 in a cradle 112 or other types of supporting structure. The self-inflating bag 102 is compressed by a curved plate 114, which is connected to a linear actuator 104, although other types or shapes of the plate 114 can be used in other examples. The signal of the actuator 104 is determined through the control unit 106 that includes a microcontroller (e.g., an Arduino microcontroller). Additionally, a reservoir bag 206 can be disposed upstream of the self-inflating bag 102.

At least one check valve 208 is provided (e.g., between the reservoir bag 206 and the self-inflating bag 102) to ensure correct flow direction. A pressure relief valve 210 disposed proximate an outlet of the self-inflating bag 102 is configured to ensure that the ventilator apparatus 100 does not exceed a specified pressure (e.g., 35 cm of water). Flowmeters 202 and 204 are provided in the inspiratory and expiratory flow paths, respectively, to measure inspired and expired air flow, which are used by the control unit 106 to manage the respiratory cycle of a patient.

In this example, the ventilator apparatus 100 also includes pressure transducers 212, 214, and 215, whose readings are collected for control and/or display via the display device 108. An exhalation pipe (not shown) also vents to the ambient through a positive end-expiratory pressure (PEEP) valve 216. The PEEP valve 216 is set to a particular value in order to help prevent a pneumothorax condition. The inspired flow rate is used to compute the total volume inspired for each breath and is checked against the set value of the PEEP valve 216.

According, the ventilator apparatus 100 includes the self-inflating bag 102 that is "squeezed" or compressed using a linear electromechanical actuator 104 that depresses the constrained self-inflating bag 102 from one side. The length and speed of the actuator 104 stroke is controlled by the control unit 106 that allows the operator to set ventilator parameters, such as BPM and TV, as described and illustrated in more detail below. The air volume delivered to and expired from the patient is measured with flowmeters 202 and 204, respectively.

In this example, a 3-way valve (not shown) (e.g., a 3-way-Duck valve) located on the self-inflating bag 102 is implemented as a flow exit with the relief valve 210 to prevent over-pressuring. The expiratory port (also referred to herein as an outlet or exit) on the self-inflating bag 102 that normally leads to a PEEP valve is plugged. A ventilator hose (not shown) can be attached to the self-inflating bag 102 flow exit and connects on the other end to a 3-way valve 200 that branches in two directions.

In particular, the 3-way valve 200 allows the passage of flow towards the inspiratory (i.e., patient) branch through a high-efficiency particulate air (HEPA) filter 218. The expired flow from the patient is directed towards the expiratory branch via the 3-way valve 200. The 3-way valve 200 passively opens the inspiratory flow path and closes the expiratory flow path when the vent hose delivers slightly pressurized flow from the self-inflating bag 102 to the 3-way valve 200 during the inspiratory phase. During the expiratory phase, the 3-way valve 200 passively opens the expiratory flow path and closes the inspiratory flow path, allowing patient exhalation.

In this particular example, the ventilator apparatus 100 also includes carbon dioxide (CO2) concentration and oxygen (O2) concentration sensors, referred to in FIG. 2 as CO2/O2 sensors 220. The CO2/O2 sensors 220 and flowmeters 202 and 204 collectively measure and provide feedback on instantaneous inspiratory and expiratory volumetric flow rate, absolute pressure at the vent line in relatively close proximity to the patient, CO2 concentration in the expiratory flow, and O2 concentration in the expiratory flow. The CO2/O2 sensors 220 and flowmeters 202 and 204 in some examples are integrated into a relatively compact electronic package connected to the control unit 106 via a wire harness that facilitated exchange of both signals to the control unit 106 and power to the CO2/O2 sensors 220 and flowmeters 202 and 204.

Accordingly, volumetric flow sensors or flowmeters are placed in the inspiratory and expiratory vent hoses. One or more of the flowmeters 202 or 204 can be a modified Venturi flowmeter designed to allow measurement of the flow in either direction (i.e., a bi-directional flow sensor). Flow is determined by measuring the static pressure drop from inlet to throat. The absolute pressure at the inlet and the pressure drop can be measured with pressure micro-sensors.

CO2 concentration in the expiratory vent hose is measured with a sensor that is based on principles of measuring light absorption by the CO2 in the air mixture, although other approaches for measuring CO2 concentration can be used. Operationally, it is necessary to draw a sample of air into the CO2 concentration sensor for measurement, which can be performed in real-time with a micro-pump attached to the exit of the CO2 concentration sensor. An O2 concentration sensor is also placed in the expiratory vent hose for measuring the O2 concentration.

Figure 3:
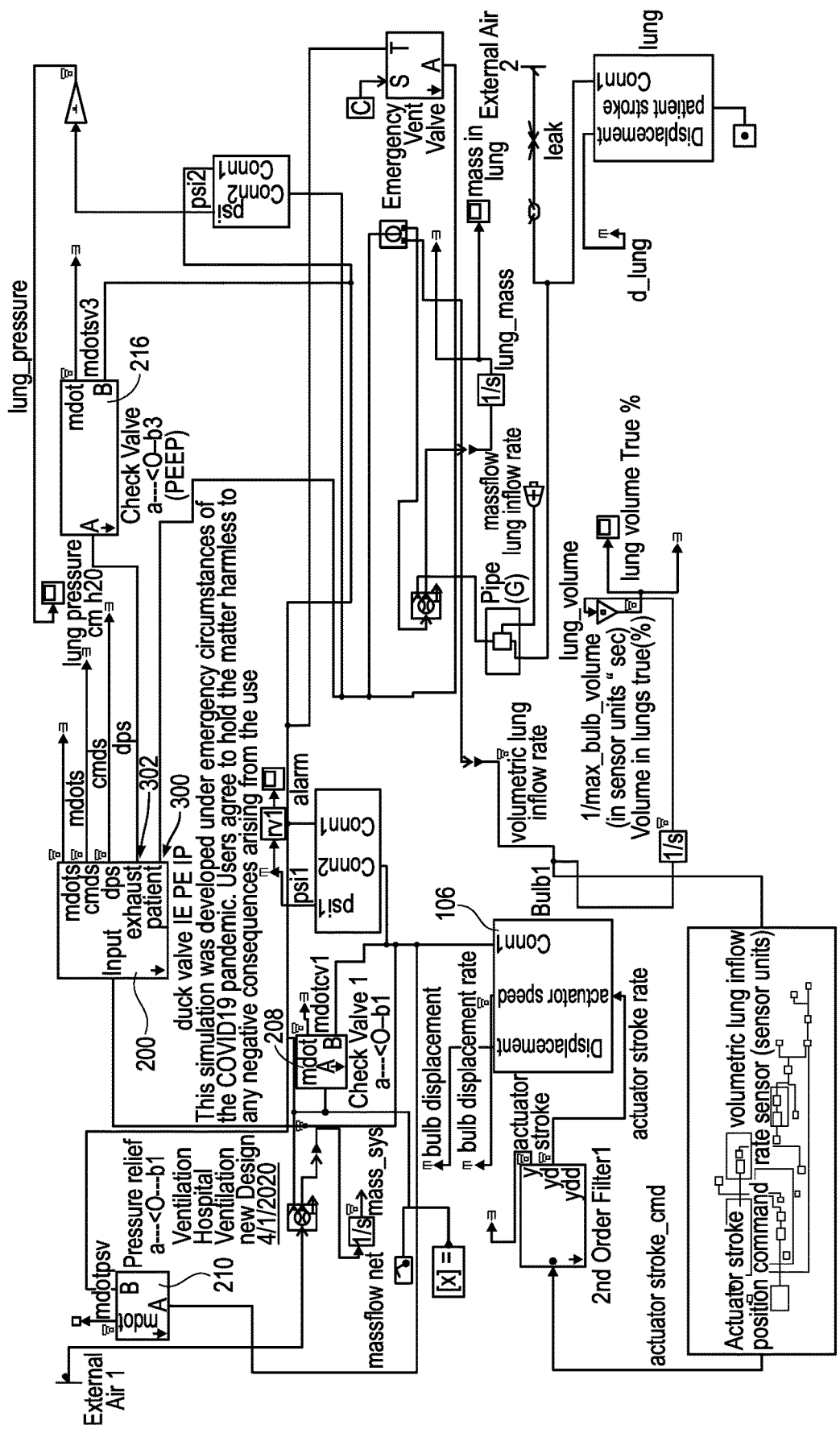
FIG. 3 is a control schematic illustrating a relationship between measured pressures and temperatures and an actuator control of a ventilator apparatus.

Referring to FIG. 3, a control schematic illustrating a relationship between measured pressures and temperatures and actuator control is illustrated. The thinner black lines are signal wires for transmitting control and sensor signals and the double black and white arrows represent the conversion of a physical quantity (such as air flow) into a signal. Signals can be displayed or otherwise output (e.g., to the display device 108) for observation by a clinician.

Starting in the upper left corner of FIG. 3, external air enters the ventilator apparatus 100. The external air flows along the line to the right, then down and to the right through an inlet check valve 208, and continues to the right toward the 3-way valve located at the exit or outlet of the self-inflating bag 102. A pressure relief valve 210, which ensures that inspiratory air pressure does not exceed a prescribed level, is connected in parallel at this point. In one example, the pressure relief valve 210 is contained within a 3-way valve whose other end is plugged. The ventilator apparatus 100 utilizes a self-inflating bag 102 or BVM with the mask removed and the components of this device, such as the bulb, are connected between the inlet check valve 208 and the 3-way valve as illustrated in FIG. 2, for example.

A second 3-way valve 200, proximate the patient, allows inspiratory air flow out of the port 300 labelled "patient" on the 3-way valve 200 when pressure on the distal side of the 3-way valve 200 exceeds pressure on the proximal side of the 3-way valve. The inspiratory air flows through a proximal flowmeter 202, a section of pipe that represents the intubation tube, and into the lungs of the patient.

The expiratory path is the reverse of the inspiratory path in this example up until the point where the air flows into the 3-way valve 200. Since the expiratory or proximal pressure now exceeds the inspiratory of distal pressure, air will flow out of the port 302 labelled "exhaust" on the 3-way valve 200, through a check valve 216, and out to ambient. The lower left quadrant of FIG. 3 illustrates the devices that are used for feedback control, culminating in signals labeled actuator stroke and actuator stroke rate. These signals represent the amount of compression on the self-inflating bag 102, which is controlled by the length of the stroke, and the rate at which the mechanical linear actuator 102 will compress the resuscitator bulb.

In order to perform the volume-based control utilized in the examples of this technology described and illustrated herein, the volume-time history of the air flow delivered to the patient during the inspiration phase of a breathing cycle is measured along with the flow rate expired by the patient during the expiration phase. To facilitate this measurement, a first flowmeter 202 is disposed upstream of the 3-way valve 200 on the inspiratory line from the self-inflating bag 102 and a second flowmeter 204 is disposed on the other leg of the 3-way valve 200, which connects the flow branch for the expiratory flow.

Figure 4:
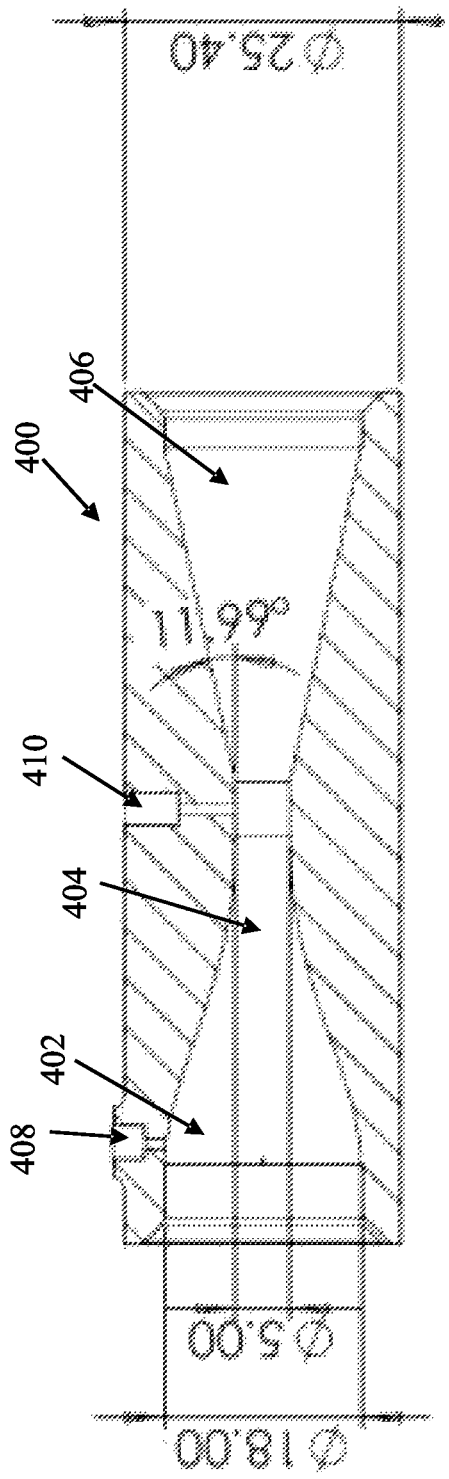
FIG. 4 is a cross-section diagram of an exemplary Venturi-style flowmeter.

The flowmeters 202 and 204 are a variation of a Venturi style flowmeter in some examples, a cross-section of which is illustrated in FIG. 4. With flow from left to right in FIG. 4, the exemplary flowmeter 400, which can be used for one or both of the flowmeters 202 and 204, has a smooth flow contraction from a larger inlet area 402 to a smaller throat area 404. In this zone, the flow accelerates from the inlet velocity to a higher velocity at the throat. The contraction is designed with a fifth order polynomial contour to prevent flow separation and assure uniform velocity at the throat. The pressure will decrease from the inlet static pressure to the static pressure at the throat, in inverse proportion to the velocity at these respective locations. The inlet velocity and volumetric flow rate can be found by measuring the static pressure drop from inlet to throat.

To obtain pressure drops in measurable ranges for the expected flows, the flowmeter 400 in one particular example has an inlet diameter of 18 mm and a throat diameter of 5 mm, although other dimensions can also be used. Beyond the throat, the flowmeter has a diffuser section 406 that allows the flow to re-expand to the exit diameter. The flowmeter 400 of FIG. 4 has a diffuser section 406 cone angle of 24° and the overall length of the flowmeter 400 is divided into equal lengths for the contraction section with the inlet area 402 and throat area 404, and the diffuser section 406, although other configurations can also be used in other examples.

As illustrated in FIG. 4, static pressure taps 408 and 410 are located at the inlet and at the throat, respectively, of the exemplary flowmeter 400. Threaded hose barbs or straight stainless-steel tubes, for example, are inserted into the taps 408 and 410 to connect tubing (e.g., plastic Tygon™) to the pressure transducers 212 and 214 in the control unit 106. On the inspiratory flowmeter, the upstream pressure and the pressure drop are transmitted to two separate pressure transducers 212 and 214 in order to record both the upstream gage pressure and the pressure drop. In order to connect the flowmeters 202 and 204 to ventilator hoses and/or the 3-way valve 200, adapters can be used (e.g., as machined from PVC).

Figure 5:
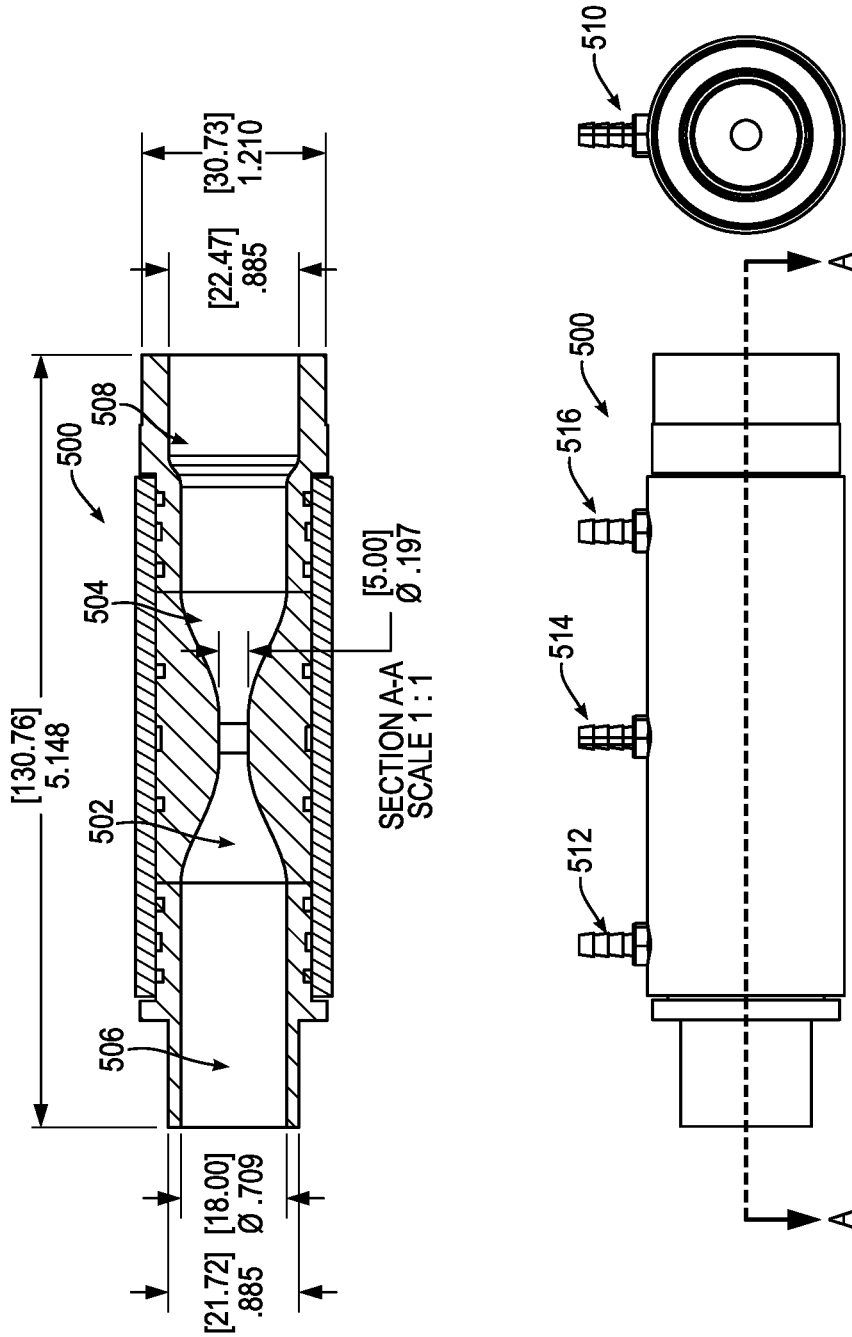
FIG. 5 is a diagram of an exemplary bi-directional flowmeter.
Figure 6B:
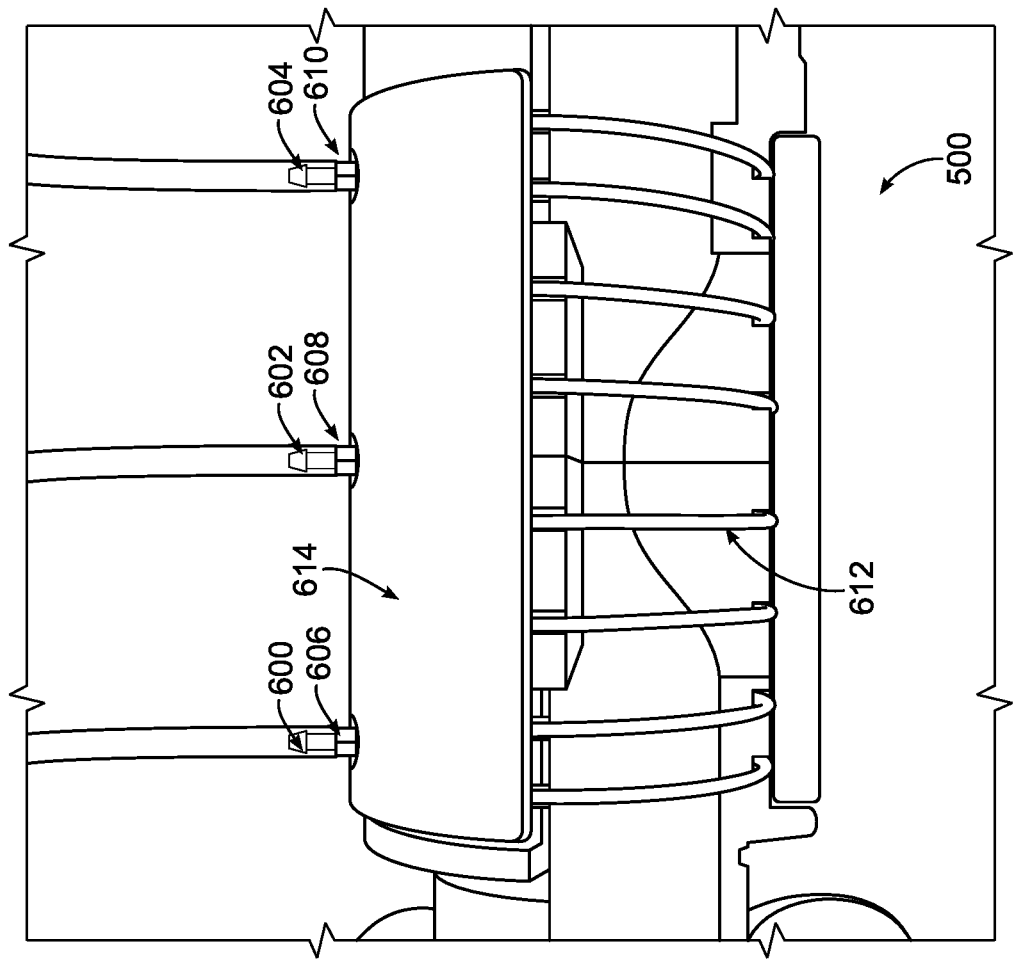
FIGS. 6A-B are external view and cross-sectional diagrams of exemplary flowmeters, respectively.
Figure 6A:
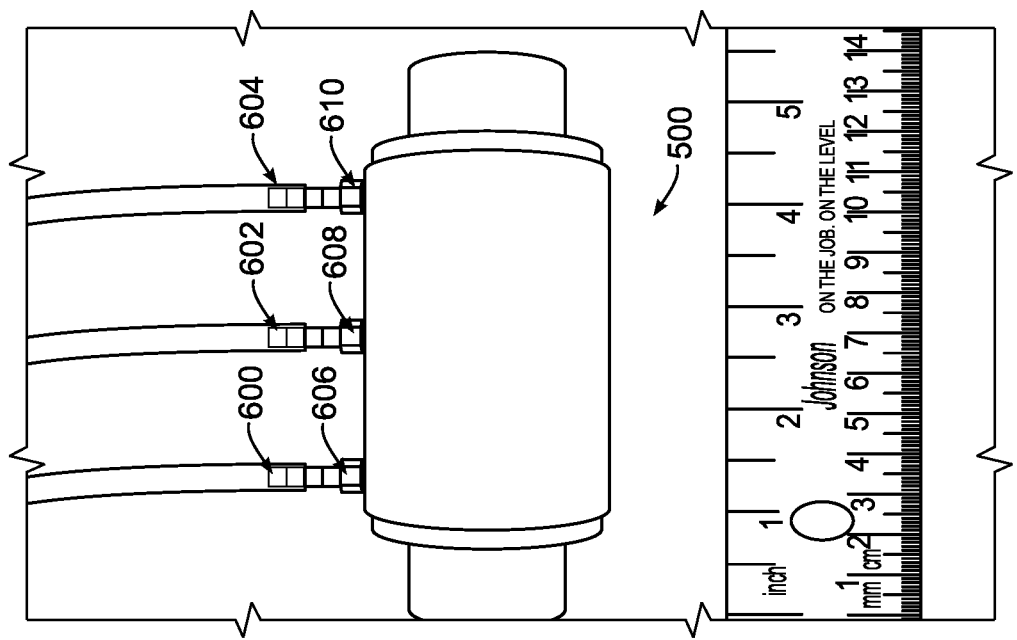

Referring to FIG. 5, a diagram of an exemplary bi-directional flowmeter a diagram of an exemplary bi-directional flowmeter 500 is illustrated. The converging section 502 and diverging section 504 of the flowmeter 500 in this particular example can be fabricated as one section, and the inlet section 506 and exit section 508 can be fabricated as separate sections, although other fabrication methods can also be used. The flowmeter 500 is bi-directional as it can be used to measure the flow from left to right or right to left, which is accomplished by replacing the conical diffuser section 406 with a reverse Venturi nozzle 510 so that the flowmeter 500 is substantially symmetrical around the throat. In order to be used in either flow direction, the flowmeter 500 has pressure taps at the inlet 512, at the throat 514, and at the exit 516.

An external view and a cross-sectional diagram of the flowmeter 500 in this example are illustrated in FIGS. 7A-7B, respectively. In this example, continuity is provided for outer pressure taps 600, 602, and 604 formed by the hose barbs 606, 608, and 6010 and the inner pressure taps 512, 514, and 516 through the inner flowmeter 500 wall. The overall length of the flowmeter 500 in this particular example is about 5 inches (127 mm), although other lengths can also be used in other examples.

Optionally, the flowmeter(s) 202 or 204 of the ventilator apparatus 100 can be fabricated using a variety of methods including machining (e.g., in PVT, aluminum) and/or 3D printing (e.g., using PLA, PC-ABS, and/or ONYX materials). In this example, the flowmeter 500 has a central converging/diverging Venturi section and separate inlet and exit connectors. The three sections are "stacked" together and inserted into an outer PVC or steel pipe section, for example. The internal sections have a set of O-rings 612 that isolate the three inner pressure taps 512, 514, and 516 so that the pressure in the zone between O-rings 606 equilibrates to the pressure in a corresponding one of the isolated inner pressure taps 512, 514, or 516. The outer casing 614 has three threaded hose barbs 606, 608, and 610 that are inserted through the casing 614 and terminate in each of the respective pressure taps 600, 602, and 604 without regard to alignment with the internal static pressure taps 512, 514, and 516.

The ventilator apparatus 100 in this example can be configured via the control unit 106 to operate in a CMV mode, wherein the principal variable to be controlled is TV. The following parameters can be set using a control panel of the control unit 106: I/E ratios selectable: presets 1:1, 1:2, 1:3; respiratory rate: from 10 to 30 breaths per minute in steps of 2; TV: 250-800 (50 ml increments); error tolerance of 10%; and inspiratory pressure limit: 15-40 cmH$_2$O in steps of 5. Although in this example the following variables are not directly set, the ventilator apparatus 100 can be configured to interface with clinical set-ups where it is possible to set one or more of the variables: PEEP: 5-20 in no more than 5 cm steps; FiO$_2$ over the range of 21% (ambient) to 90% of the source oxygen concentration input to the ventilator apparatus 100 in no more than 10% steps.

The ventilator apparatus 100 receives signal values from the flowmeters 202 and 204 that enable it to determine inspiratory and expiratory pressures and flow rates in this example. The control panel is connected to the microcontroller and sends the set values of I/E ratio, BPM, and required TV, which is used to determine inhalation and exhalation times. Based on this data, the actuator is given a control input using a proportional-integral-derivative (PID) control law with optimized gains, for example. The sensed flow velocity is integrated to determine the TV delivered, which is used as a control variable to retract the linear actuator 104 when the set point is reached.

In other examples, the ventilator apparatus 100 can be configured via the control unit 106 to operate in a Synchronized Intermittent Mandatory Ventilation (SIMV) mode in which the pressure sensor (e.g., pressure transducer 212) is monitored for a sudden decrease in pressure that corresponds to the patient inhaling. At that point, a PID controller maintains a constant pressure to support the patient's own breath. In yet other examples, the ventilator apparatus 100 can be configured for other modes of operation.

Figure 7:
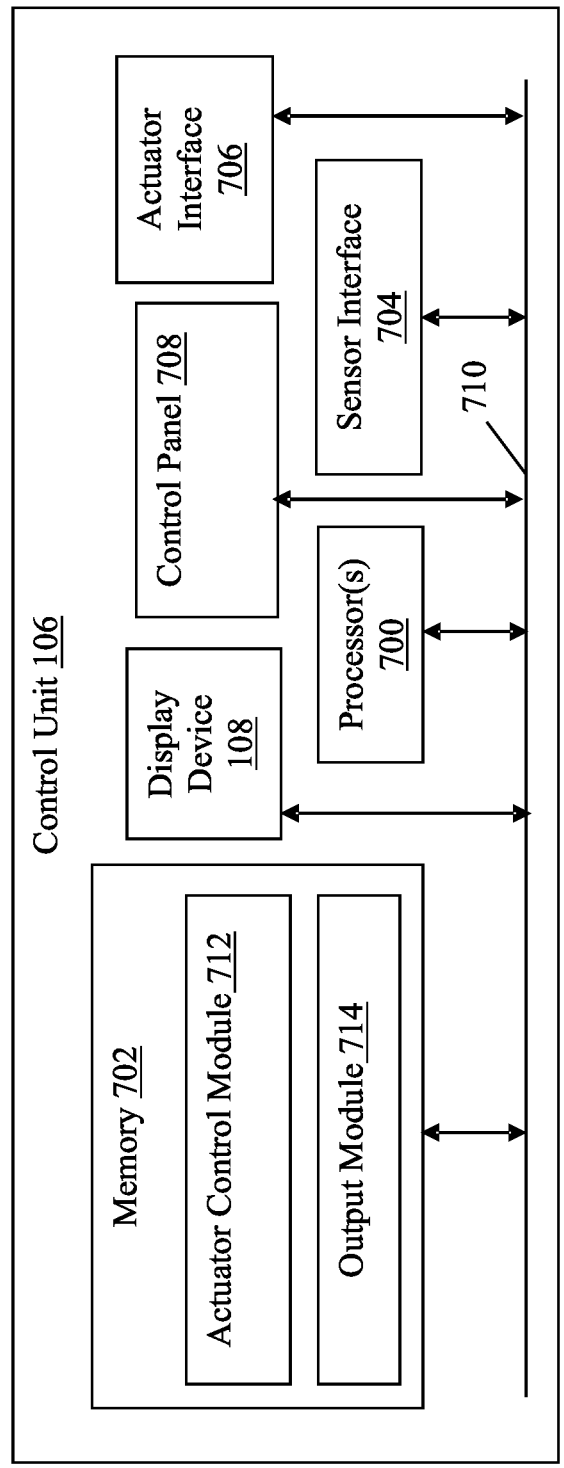
FIG. 7 is a block diagram of an exemplary control unit of a ventilator apparatus.

Referring to FIG. 7, a block diagram of an exemplary control unit 106 of the ventilator apparatus 100 is illustrated. In this particular example, the control unit 106 includes processor(s) 700, a memory 702, a sensor interface 704, an actuator interface 706, a control panel 708, and a display device 108, which are coupled together by a bus 710 or other communication link, although the control unit 106 can include other types and/or numbers of systems, devices, components and/or other elements in other configurations. Optionally, the components of the control unit 106 illustrated in FIG. 7 are housed within a control unit enclosure, such as the enclosure 110 illustrated in FIG. 1, for example.

The processor(s) 700 of the control unit 106 may execute programmed instructions stored in the memory 702 of the control unit 106 for the any number of the functions and other operations illustrated and described herein. The processor(s) 700 may include one or more CPUs or general purpose processors with one or more processing cores, for example, although other types of processor(s) can also be used. In other examples, the processor(s) 700 can include a microcontroller, a reduced instruction set architecture (RISC) processor, configurable hardware logic (e.g., a field programmable gate array (FPGA), and/or any combination of such processing devices. Accordingly, while processor(s) 700 and separate memory 702 coupled via a bus 710 are included in the example illustrated in FIG. 7 and described herein, other architectures can also be used.

The memory 702 of the control unit 106 stores the programmed instructions for one or more aspects of the present technology as described and illustrated herein, although some or all of the programmed instructions could be stored elsewhere. A variety of different types of memory storage devices, such as random access memory (RAM), read only memory (ROM), flash memory, or other computer readable medium which is read from and written to by a magnetic, optical, or other reading and writing system that is coupled to the processor(s) 700, can be used for the memory 702. The memory 702 of the control unit 106 can store one or more applications that can include executable instructions that, when executed by the processor(s) 700, cause the control unit 106 to perform actions, such as to communicate with the flowmeters 202 and 204 and/or control the linear actuator 104, for example, and to perform other actions as described and illustrated by way of the examples herein.

Accordingly, the examples may also be embodied as one or more non-transitory computer readable media, such as the memory 702 of the control unit 106, having instructions stored thereon for one or more aspects of the present technology as described and illustrated herein. The instructions in some examples include executable code that, when executed by one or more processing devices, such as the processor(s) 700 of the control unit, cause the processing devices to carry out steps necessary to implement the methods of the examples of this technology that are described and illustrated herein.

The memory 702 of the control unit 106 in these particular examples includes an actuator control module 712 and an output module 714. The actuator control module 712 is configured to process input from the control panel 708 and sensors (e.g., flowmeters 202 and 204 and pressure transducers 212 and 214) to selectively extend and retract the linear actuator 104 using control signals sent via the actuator interface 706. The output module 714 is configured to communicate sensed or determined parameters to the display device 108, as described and illustrated in more detail below. The display device 108 can be an LED display, for example, although other types of displays can also be used in other examples.

The sensor interface 704 of the control unit 106 operatively couples and communicates with the various sensors of the ventilator apparatus 100, including the flowmeters 202 and 204, pressure transducers 212 and 214, and/or CO2/O2 sensors 220. Accordingly, the sensor interface 704 obtains signals from the sensors that are communicated to the actuator control module 712 to facilitate determination of pressures and flow rates, for example. The actuator interface 706 of the control unit 106 couples and communicates with the linear actuator 104 by issuing control signals that selectively cause the linear actuator 104 to extend or retract, for example, as described and illustrated in more detail below. While a linear actuator 104 is described and illustrated herein, other types of actuation mechanisms and devices can also be used in other examples.

Figure 8:
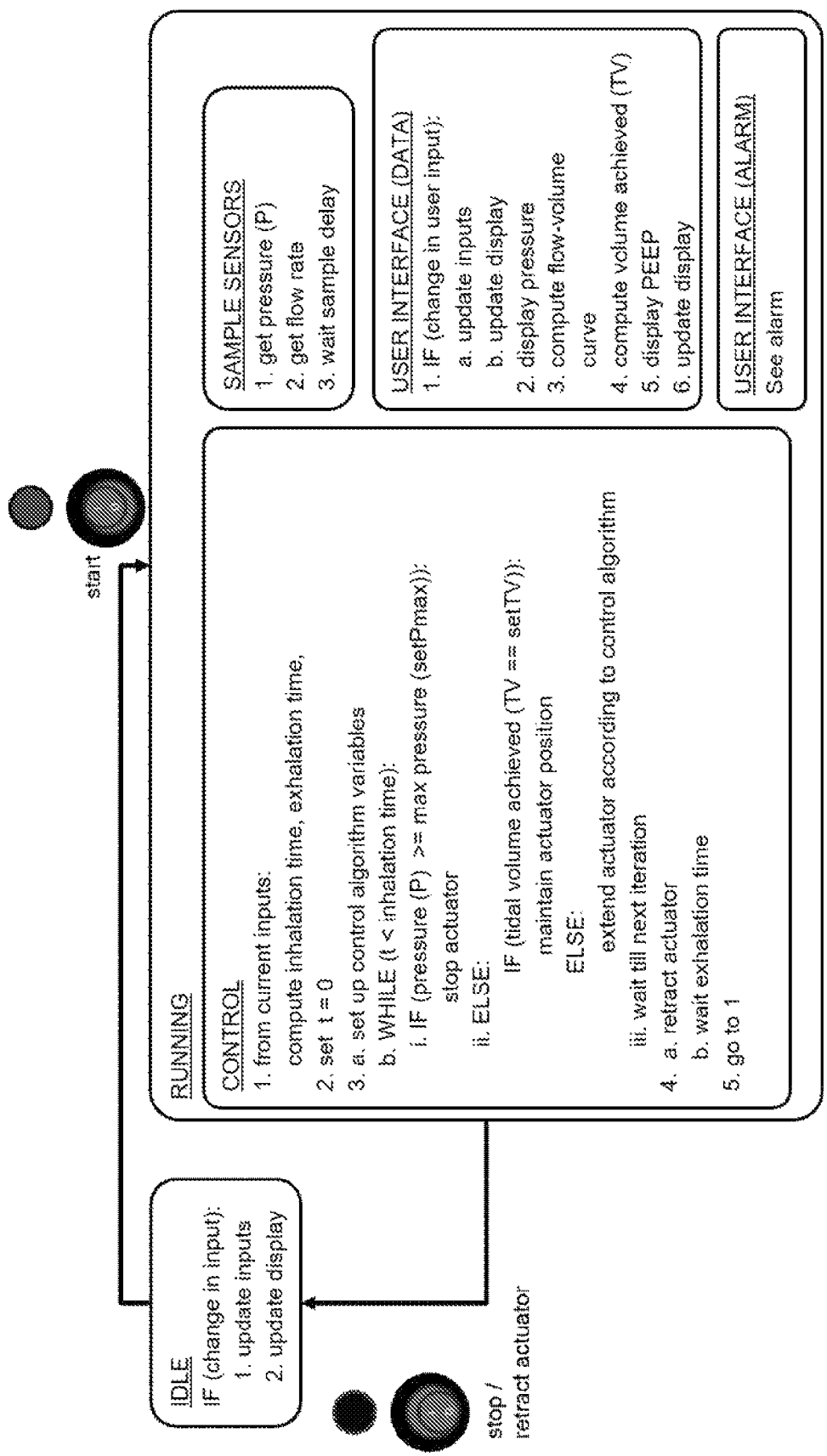
FIG. 8 is a flow diagram of an exemplar method of operation of a control unit of a ventilator apparatus.

Referring to FIG. 8, a flow diagram of an exemplary method of operation of the control unit 106 of the ventilator apparatus 100 is illustrated. In a first step in this example, the control unit 106 obtains ventilator parameter values via the control panel 708. The ventilator parameter values in this example include at least an inspiratory pressure limit (referred to in FIG. 8 as setPmax), BPM, and required TV (referred to in FIG. 8 as setTV), although other parameter values can also be obtained in other examples.

In a second step, the control unit 106 sets or specifies the inhalation time and exhalation time based on the ventilator parameter values obtained in the first step. The inhalation time and exhalation time are used to facilitate control of the linear actuator 104.

In a third step, the control unit 106 resets a timer. The timer is set to zero, for example, and is compared to the inhalation time in order to effectively define the respiratory cycle.

In a fourth step, the control unit 106 obtains a current inspiratory pressure and a current TV (referred to in FIG. 8 as tidal volume achieved) via signal values from the flowmeters 202 and 204 and/or pressure transducers 212 and 214. The control unit 106 can optionally also obtain a current expiratory pressure and can calculate a current I/E ratio based on the current inspiratory and expiratory pressures. Also optionally, the control unit 106 can output one or more of the current inspiratory pressure, a current expiratory pressure, current I/E ratio, or flow rate on the display device 108 to facilitate monitoring by a clinician.

In a fifth step, the control unit 106 determines whether the timer value is less than the inhalation time set in the second step. In a first iteration, the timer value will always be less than the inhalation time. If the control unit 106 determines that the timer value is less than the inhalation time, then the control unit 106 proceeds to a sixth step.

In the sixth step, the control unit 106 determines whether the current inspiratory pressure is greater than or equal to the inspiratory pressure limit obtained in the first step. If the current inspiratory pressure is greater than or equal to the inspiratory pressure limit, then the control unit 106 in a seventh step sends a control signal to the linear actuator 104 to stop the linear actuator 104. However, if the control unit 106 determines that the current inspiratory pressure is not greater than or equal to the inspiratory pressure limit, then the control unit 106 proceeds to an eighth step.

In the eighth step, the control unit 106 determines whether the current TV is equivalent to the TV obtained in the first step. If the current TV is equal to the TV obtained in the first step, then the control unit 106 in a ninth step maintains the current linear actuator 104 position by not sending any additional control signals to the linear actuator 104. However, if the control unit 106 determines in the eighth step that the current TV is not equal to the TV obtained in the first step, then the control unit 106 proceeds to a tenth step.

In the tenth step, the control unit 106 generates and sends a control signal to the linear actuator 104 to cause the linear actuator 104 to extend, optionally according to a control algorithm established before initiation of the respiratory cycle. The control algorithm can define the rate and length/distance at which the linear actuator 104 is extended and/or retracted, for example. By extending the linear actuator 104, the plate 106 compresses the self-inflating bag 102 of the ventilator apparatus 100 as part of an inspiratory phase of a respiratory cycle.

Subsequent to extending the linear actuator 104 according to the control algorithm, the control unit 106 proceeds back to the fifth step and again determines whether the timer value is less than the inhalation time. If in this iteration, the control unit 106 determines that the timer value is not less than the inhalation time, then the control unit 106 proceeds to an eleventh step.

In the eleventh step, the control unit sends a control signal to the linear actuator 104 to cause the linear actuator 104 to retract and thereby allow the self-inflating bag 102 to re-inflate during an expiratory phase of the respiratory cycle. The control unit 106 then determines whether the exhalation time has expired, such as based on a comparison of the exhalation time with the timer. If the exhalation time has expired, then the control unit 106 proceeds back to the first step in this example. In other examples, the first step can be skipped on second and subsequent iterations when a determination indicates that there are no changes in inputs.

Figure 9:
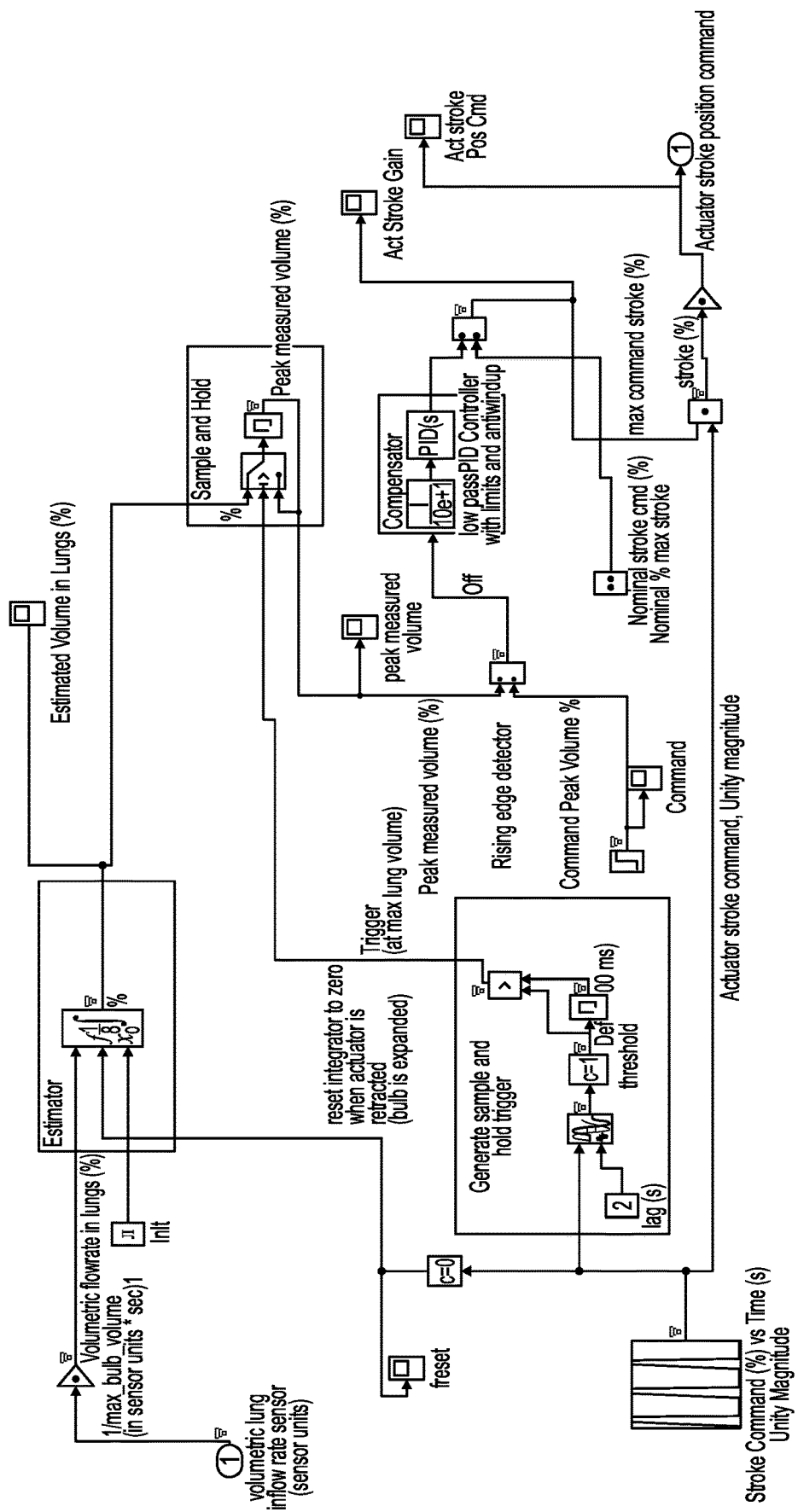
FIG. 9 is a schematic of an exemplary microcontroller of a ventilator apparatus.

Referring to FIG. 9, a schematic of an exemplary microcontroller of the ventilator apparatus 100 is illustrated. The microcontroller can be used in combination with, or in place of, the control unit 106 and is configured to monitor the flow of air into the lungs and uses that signal to estimate the volume of air delivered, which allows for control of air volume on each cycle of the ventilator apparatus 100. The microcontroller outputs a position command (e.g., the linear actuator stroke position command of FIG. 3) to the linear actuator 104 in order to control compression of the bulb of the self-inflating bag 102 for each cycle.

Figure 10:
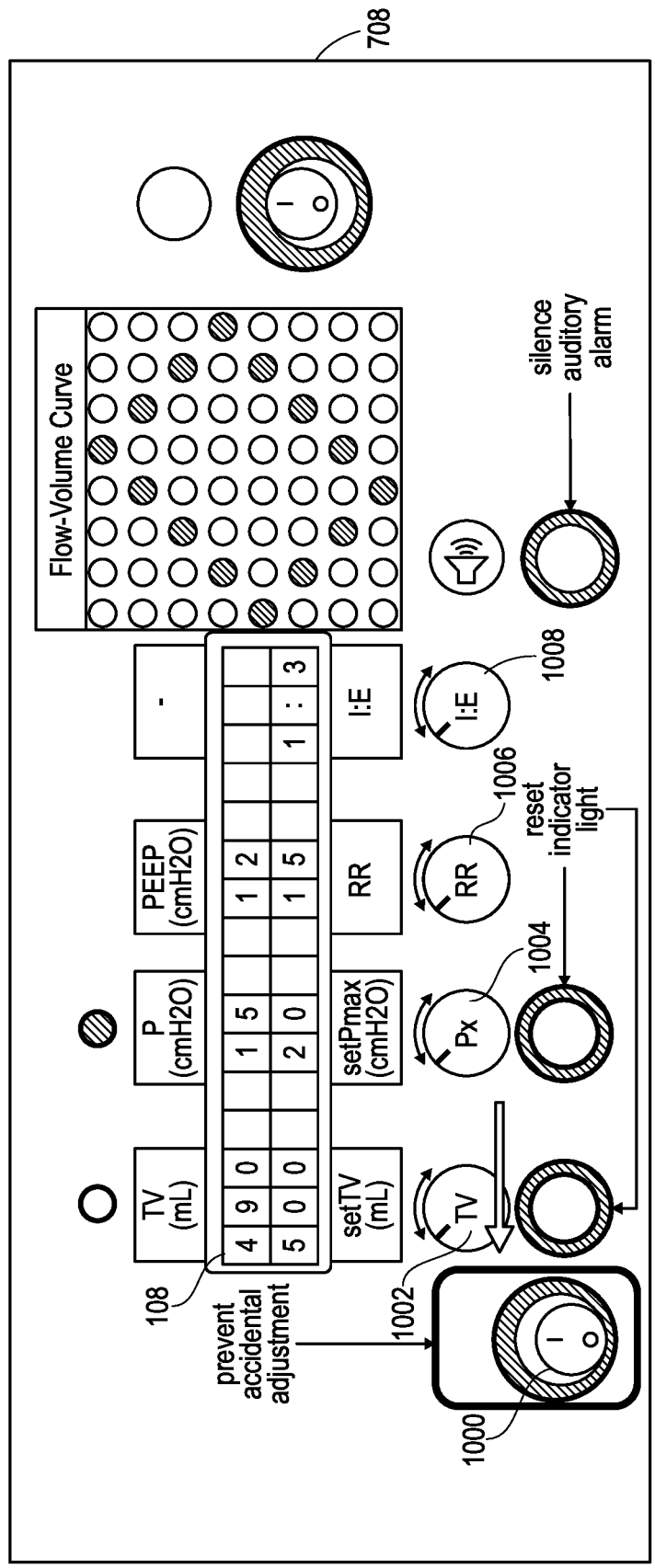
FIG. 10 is an exemplary control panel of a ventilator apparatus.

Referring to FIG. 10, exemplary instructions for use of the ventilator apparatus 100 will now be described with reference to an exemplary control panel 708. In a first step illustrated in FIG. 10, a user of the ventilator apparatus 100 turns the ventilator apparatus 100 on and presses the bottom portion of the lock/unlock switch 1000 down to the '0' setting, to unlock the controls. In this example, once controls are set, they can be locked to prevent accidental adjustment by pressing the lock/unlock switch 1000 to "I" to lock controls; In order to adjust the settings the lock/unlock switch 1000 must be turned down to "0" to unlock. The lock/unlock switch 1000 can be disposed on the control panel 708 of the control unit 106, for example.

In a second step, a user of the ventilator apparatus 100 sets the tidal volume to a desired level by turning TV dial 1002 right to increase or left to decrease. The set tidal volume then optionally appears in mLs on a bottom row of the display device 108 of the control panel 708.

In a third step, a user of the ventilator apparatus 100 sets a maximum pressure to a desired level, using the Px control knob 1004. Optionally, the set maximum pressure in cmH2O is then displayed on the bottom row of the display device 108 of the control panel 708 in a second column.

In a fourth step, a user of the ventilator apparatus 100 sets a respiration rate to a desired level, using the RR control knob 1006. In this example, the respiratory rate or "RR" can be set to the patient's breath rate per minute (BPM) by turning the RR control knob 106 right to increase or left to decrease. Optionally, the set RR in BPM is output to the bottom row of the of the display device 108 of the control panel 708.

In a fifth step, a user of the ventilator apparatus 100 sets an inspiratory to expiratory ratio (I:E) to a desired level, using the I:E control knob 1008. Optionally, the set I:E ratio appears on the bottom row of the display device 108 of the control panel 708 in a fourth column. Accordingly, subsequent to the fifth step, the patient variables are output in the top row of the display device 108 from left to right: tidal volume or TV (mL); pressure or P (cmH2O); and PEEP (cmH2O) (based on the PEEP valve 216 on expiratory limb).

In some examples, the display device 708 of the control unit 106 of the ventilator apparatus 100 can output current settings (inspiratory pressure, tidal volume, and/or frequency) and/or current delivery parameters (inspiratory pressure, tidal volume, and/or respiratory rate). PEEP and $FiO_2$ settings are not output by the display device 708 in some examples, but are available through inspection and can be output in other examples. Additionally, the control unit 106 can include an LED array (e.g., an 8×8 LED array) via which a flow rate vs. volume graph is output. Additionally, the display device 708 can be configured to display CO2 and/or O2 concentration communicated via the CO2/O2 sensors 220.

Figure 11A:
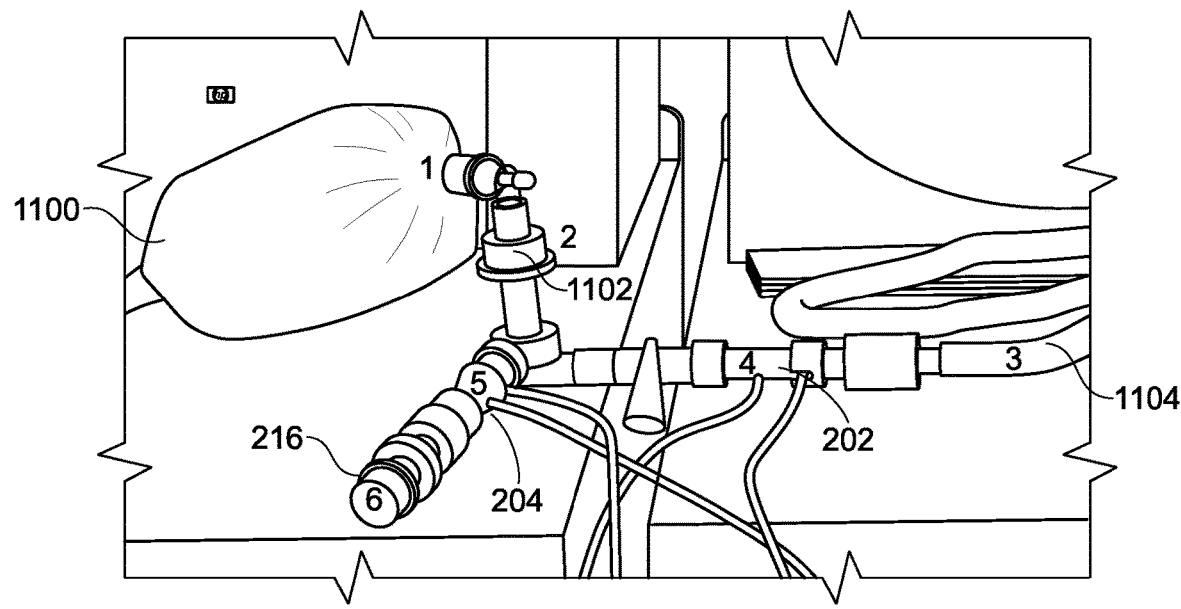
FIGS. 11A-B are diagrams of a ventilator apparatus coupled to a patient at an endotracheal tube connection.
Figure 11B:
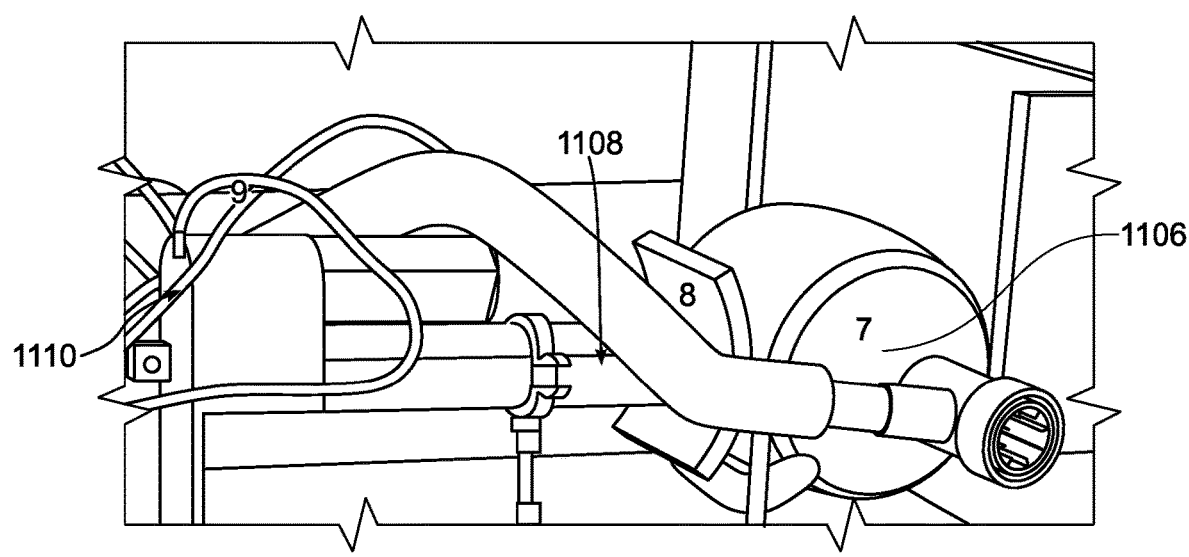

In a sixth step illustrated in FIGS. 11A-11B, the ventilator apparatus 100 is coupled to a patient at the patient's ETT connection. In particular, the patient end of the ventilator apparatus 100 is illustrated in FIG. 11A and the BVM compressor of the exemplary ventilator apparatus 100 is illustrated in FIG. 11B with the following components: Mapleson bag 1100 represents patient lungs; HME filter/viral/bacterial filter 1102; patient system 1104—connects to BVM or self-inflating bag 102; inspiratory flowmeter 202; expiratory flowmeter 204; PEEP valve 216; BVM ventilation system 1106; BVM compressor 1108; and power cables 1110.

In some examples, the ventilator apparatus 100 of this technology provides ventilation at a patient-connection port within alarm limits set by an operator, and/or informs the operator via an alarm condition that ventilation within the alarm limits is not occurring. Alarm notifications can be a combination of sounds and lights, for example. Such alarm conditions include the following in some examples: (1) ventilator not delivering because of gas or electricity supply failure or the ventilator is switched off, or there is a loose or broken connection; (2) inspiratory airway pressure exceeded (3) inspiratory pressure not achieved (equivalent to disconnection alarm condition); and/or (4) tidal volume not achieved or exceeded. Other alarm conditions and/or notifications can also be used in other examples.

Referring to FIG. 12, exemplary alarm outputs of the ventilator apparatus 100 are illustrated via the control panel 708. In this particular example, the buttons 1200 represent alarm reset buttons. The first button 1202 correlates with a tidal volume alarm reset. The first alarm light 1204 is illuminated when the tidal volume is less than 20% of the set tidal volume for more than five breaths. This alarm can be reset by pushing the first button 1202. The second button 1204 in this example correlates with a pressure high alarm. The second alarm light 1206 is illuminated when the pressure is greater than the set max pressure. This alarm can be reset by pushing the second button 1204. The third button 1208 represents an alarm silence button in this example. In other examples, other types of buttons, switches, and interface elements facilitating other functionality can also be used on the control panel 708.

Referring to FIGS. 13A-D, tables of exemplary failure scenarios and resulting actions, including particular triggered alarm(s), relating to the bag-mask-valve gas inlet, mechanical air-pump outlet, inspiration line outlet, and expiration line outlet, respectively, are illustrated. Failure of any of the components of the ventilator apparatus 100 in some examples is handled in a manner that puts the ventilator apparatus 100 out of operation and/or sounds an alarm to request manual intervention.

Referring to FIG. 14, a table including exemplary components of the ventilator apparatus 100 is illustrated. In this example, component descriptions are identified along with the material, vendor, part number, and quantity, although different components, materials, vendors, and/or part numbers can be used in other examples.

Figure 15:
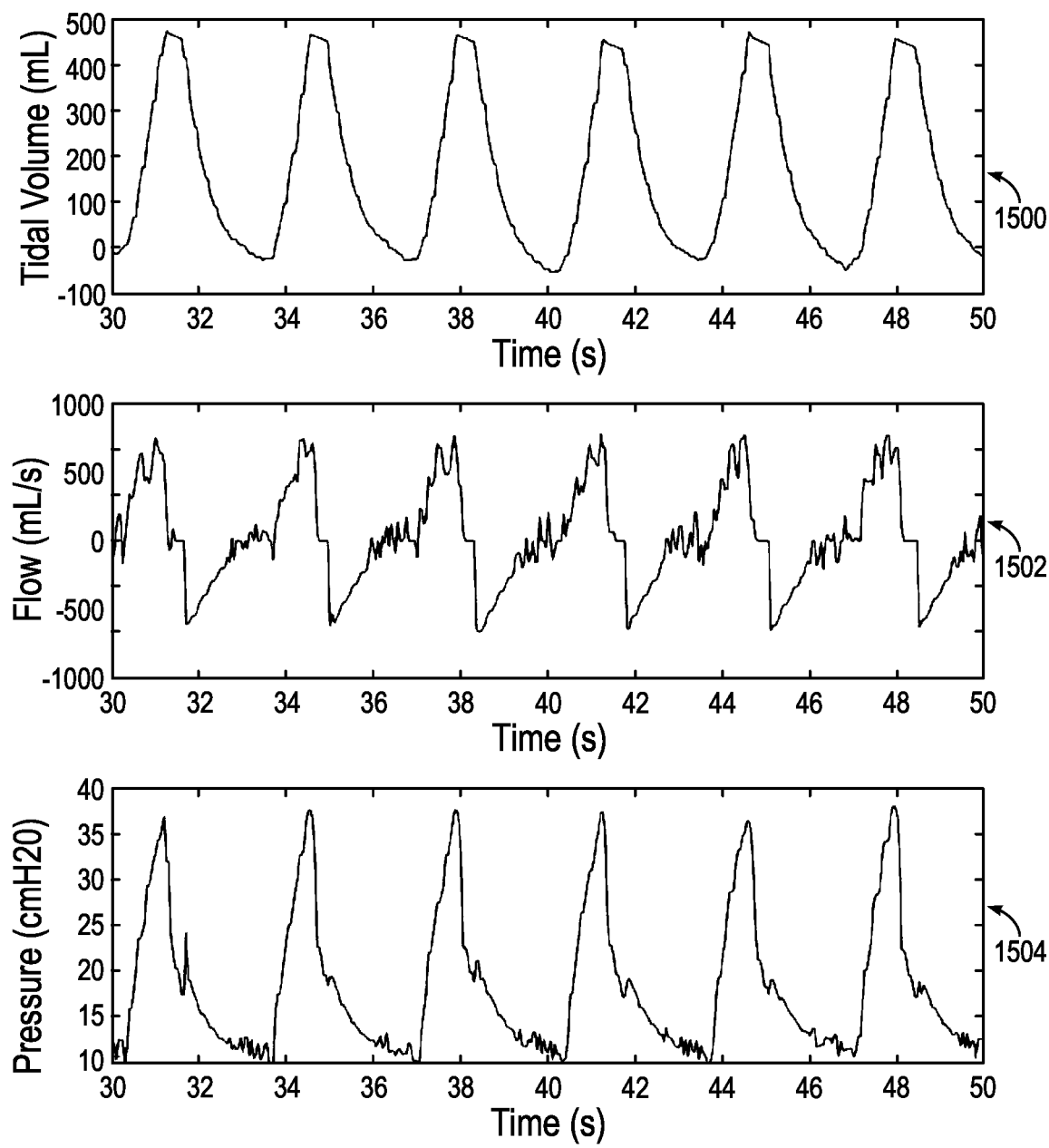
FIG. 15 is a set of graphs of exemplary testing results for a ventilator apparatus.

Referring to FIG. 15, a set of graphs 1500, 1502, and 1504 of exemplary testing results for the ventilator apparatus 100 is illustrated. The ventilator apparatus 100 of this technology was tested in a laboratory with a breathing lung simulator to determine control variables for the linear actuator 104. The key variables in this example were pressures, flow rates, and volumes. Sample data for RR=18, I/E=1:2, and TV=500 is illustrated with respect to TV, flow, and pressure over time in graphs 1500, 1502, and 1504, respectively.

Figure 16C:
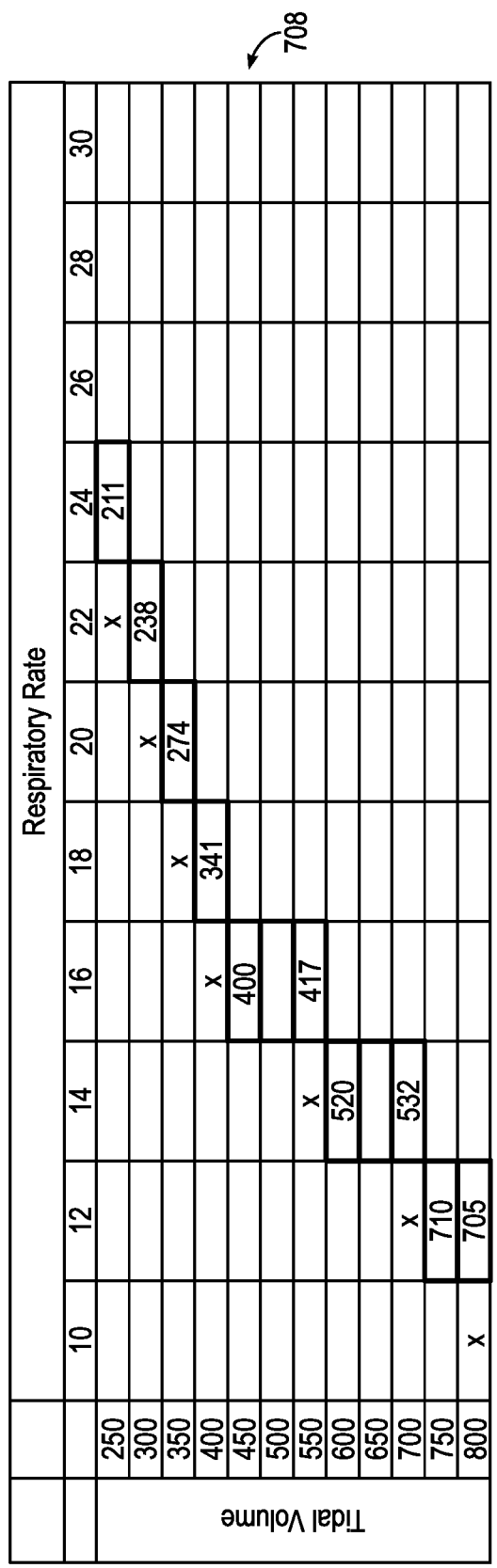

FIGS. 16A-C, graphs 1600, 1602, and 1604 of exemplary performance of the ventilator apparatus 100 with respect to respiratory rate and tidal volume is illustrated. In particular, the performance of the ventilator apparatus 100 for I:E ratio of 1:1, 1:2 and 1:3 is illustrated in graphs 1600, 1602, and 1604, respectively. The rows in the graphs 1600, 1602, and 1604 in these examples represent the respiratory rates and the columns represent tidal volumes. The lighter shaded boxes illustrated all combinations that are possible with the ventilator apparatus 100. The 'x' marks specific tests where detailed data was collected, and the darker shaded boxes indicate where the ventilator apparatus 100 was not able to deliver the set tidal volume. The numbers in the darker shaded squares record the actual volumes that were achieved. The pass condition was defined as being able to achieve the set tidal volume within plus or minus 25 cc, and all numbers were averaged over three cycles.

As described and illustrated by way of the example herein, this technology provides a relatively low-cost ventilator apparatus that can be manufactured relatively quickly with a reduced number of parts, while including alarms, safety shutoffs, and functional displays to enable effective and safe use in a clinical environments. The ventilator apparatus of this technology is advantageously capable of emergency use to improve outcomes for severely ill patients in underserved populations that are unable to breathe on their own due to a viral infection, for example.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A ventilator apparatus, comprising:
a linear electro-mechanical actuator configured to operatively interface with a self-inflating bag that comprises an inlet configured to receive air and an outlet configured to expel the received air;
a three-way valve coupled to the outlet of the self-inflating bag via a first flowmeter in an inspiratory flow path, an ambient environment via an expiratory flow path, and a patient via an endotracheal tube, wherein the three-way valve is directly coupled to the first flowmeter, which is directly coupled to one or more pressure transducers in the inspiratory flow path, and the first flowmeter is upstream of the three-way valve in the inspiratory flow path;
a control unit communicably coupled to the linear electro-mechanical actuator and, via a first one of the pressure transducers, the first flowmeter and comprising a control panel, memory comprising programmed instructions stored thereon, and one or more processors configured to execute the stored programmed instructions to:
set an inhalation time and an exhalation time based on parameter values obtained via the control panel;
obtain at least a current inspiratory pressure from the one or more pressure transducers, wherein the one or more pressure transducers are coupled between the control unit and the flowmeter; and
selectively control a stroke of the linear electro-mechanical actuator, based on the inhalation and exhalation times and a comparison of the current inspiratory pressure with one or more of the parameter values, to facilitate inspiratory and expiratory phases of a respiratory cycle for the patient.

2. The ventilator apparatus of claim 1, further comprising:
a cradle configured to receive the self-inflating bag; and
a curved plate coupled to the linear electro-mechanical actuator and configured to engage with, and disengage from, the self-inflating bag in the cradle based on the stroke of the linear electro-mechanical actuator.

3. The ventilator apparatus of claim 1, further comprising a reservoir bag, a check valve disposed between the inlet of the self-inflating bag and the reservoir bag, and a pressure relief valve disposed between the outlet of the self-inflating bag and the first flowmeter.

4. The ventilator apparatus of claim 3, wherein:
the ventilator apparatus is configured to receive air between the reservoir bag and the check valve and the check valve is configured to ensure correct flow direction of the air; and
the pressure relief valve is configured to ensure that the ventilator apparatus does not exceed a defined pressure limit.

5. The ventilator apparatus of claim 1, wherein at least a second one of the pressure transducers comprises a differential pressure transducer.

6. The ventilator apparatus of claim 1, further comprising a positive end-expiratory pressure (PEEP) valve disposed between an exhalation pipe that vents to an ambient environment and a second flowmeter in the expiratory flow path.

7. The ventilator apparatus of claim 1, further comprising a high-efficiency particulate air (HEPA) filter disposed between the three-way valve and the endotracheal tube that is coupled to the patient.

8. The ventilator apparatus of claim 1, wherein one or more of the first flowmeter or a second flowmeter in the expiratory flow path operates according to the Venturi effect and comprises:
an inlet section comprising an inlet converging section, a throat section comprising a smaller diameter than the inlet section, and a diffuser section comprising an exit and a larger diameter than the throat section; and
first and second static pressure taps disposed proximate the inlet section and the throat, respectively, and coupled to tubing that is coupled to at least one of the pressure transducers, wherein the first and second static pressure taps are configured to facilitate measurement of a pressure difference between the inlet section and the throat.

9. The ventilator apparatus of claim 8, wherein the diffuser section comprises a conical diffuser.

10. The ventilator apparatus of claim 1, wherein the first flowmeter or a second flowmeter in the expiratory flow path comprises a bidirectional flowmeter having a throat section disposed between an inlet section and a diffuser section and a static pressure tap disposed proximate the diffuser section.

11. The ventilator apparatus of claim 1, wherein the first flowmeter or a second flowmeter in the expiratory flow path comprises a throat section disposed between an inlet section and a diffuser section, the one or more of the first flowmeter or the second flowmeter further comprises separate inlet and exit connectors, and one or more of the inlet, throat, or diffuser sections are configured to be stacked together and inserted into an outer pipe section.

12. The ventilator apparatus of claim 8, wherein the one or more of the first flowmeter or the second flowmeter further comprises a throat section comprising O-rings that each isolate one of the static pressure taps to facilitate equilibration of pressure in zones between the O-rings to pressure in at least one of the static pressure taps and allow for threaded hose barbs to be inserted through a casing and terminate in each of the zones irrespective of alignment with the static pressure taps.

13. The ventilator apparatus of claim 10, wherein the diffuser section comprises a reverse Venturi nozzle.

14. The ventilator apparatus of claim 11, wherein the throat section comprises a converging/diverging Venturi section.

15. A method for facilitating a respiratory cycle, the method implemented by a control unit of a ventilator apparatus and comprising:
setting an inhalation time and an exhalation time based on obtained parameter values comprising at least an inspiratory pressure limit and a required tidal volume;
obtaining at least a current inspiratory pressure from one or more pressure transducers coupled to the control unit and directly to a flowmeter, wherein the flowmeter is coupled directly to a three-way valve, upstream of the three-way valve in an inspiratory flow path, and disposed between a self-inflating bag and the three-way valve in the inspiratory flow path; and
selectively controlling a stroke of a linear electro-mechanical actuator, based on the inhalation and exhalation times and a comparison of the current inspiratory pressure with one or more of the parameter values, to facilitate inspiratory and expiratory phases of a respiratory cycle for a patient.

16. The method of claim 15, further comprising extending the linear electro-mechanical actuator based on a control algorithm when a current tidal volume is unequal to the required tidal volume, the current inspiratory pressure is less than the inspiratory pressure limit, and an elapsed time since initiation of an inspiratory phase of the ventilator apparatus is less than the inhalation time.

17. The method of claim 15, further comprising stopping the linear electro-mechanical actuator when the current inspiratory pressure is greater than or equal to the inspiratory pressure limit and an elapsed time since initiation of an inspiratory phase of the ventilator apparatus is less than the inhalation time.

18. The method of claim 15, further comprising maintaining a position of the linear electro-mechanical actuator when a current tidal volume is equal to the required tidal volume, the current inspiratory pressure is less than the inspiratory pressure limit, and an elapsed time since initiation of an inspiratory phase of the ventilator apparatus is less than the inhalation time.

19. The method of claim 15, further comprising outputting an alarm notification when an alarm condition is determined to have occurred based on exceeding an alarm limit, a power supply failure, or one or more monitored pressures, flow rates, or volumes.

20. The method of claim 15, further comprising:
retracting the linear electro-mechanical actuator when an elapsed time since initiation of an inspiratory phase of the ventilator apparatus is greater than or equal to the inhalation time; and obtaining at least another current inspiratory pressure and another current tidal volume in a subsequent iteration upon expiration of the exhalation time.

21. A method of making a ventilator apparatus, the method comprising:
placing a self-inflating bag into a cradle disposed within an enclosure, wherein the self-inflating bag comprises an inlet configured to receive air and an outlet configured to expel the received air;

coupling a three-way valve to the outlet of the self-inflating bag via a flowmeter in an inspiratory flow path, an ambient environment via an expiratory flow path, and a patient via an endotracheal tube in the inspiratory flow path;

inserting one or more pressure transducers into the flowmeter, wherein the flowmeter is coupled directly to the three-way valve and is upstream of the three-way valve in the inspiratory flow path;

attaching a linear electro-mechanical actuator to the enclosure proximate the self-inflating bag, wherein the linear electro-mechanical actuator is configured to operatively engage with, and disengage from, the self-inflating bag; and communicably coupling a control unit to the linear electro-mechanical actuator and the one or more pressure transducers, wherein the control unit is configured to selectively control a stroke of the linear electro-mechanical actuator to facilitate inspiratory and expiratory phases of a respiratory cycle for a patient.

\* \* \* \* \*